United States Patent [19]
Maes et al.

[11] Patent Number: 6,136,270
[45] Date of Patent: Oct. 24, 2000

[54] CAROUSEL FOR INCUBATION STATION

[75] Inventors: Gregory R. Maes, Fenton; Dennis M. Connor, St. Charles; Brent D. Freiner, St. Charles; Clifford W. Karl, St. Charles; Ron Robinson, Bridgeton; Raymond M. Shelton, St. Charles; Garry R. Tegeler, Hazelwood; Michael James Justin, St. Louis, all of Mo.

[73] Assignee: bioMérieux, Inc., Hazelwood, Mo.

[21] Appl. No.: 09/300,751

[22] Filed: Apr. 26, 1999

Related U.S. Application Data

[60] Division of application No. 08/905,374, Aug. 4, 1997, which is a continuation-in-part of application No. 08/604,672, Feb. 21, 1996, Pat. No. 5,762,873.

[51] Int. Cl.[7] .................................................. G01N 35/00
[52] U.S. Cl. ........................... 422/64; 422/63; 422/104; 436/43; 436/46
[58] Field of Search ............................... 422/63, 64, 104; 436/43, 46, 45, 47

[56] References Cited

U.S. PATENT DOCUMENTS

| | | |
|---|---|---|
| 4,038,151 | 7/1977 | Fadler . |
| 4,116,775 | 9/1978 | Charles . |
| 4,118,280 | 10/1978 | Charles et al. . |
| 4,219,529 | 8/1980 | Tersteeg et al. .................... 422/65 |
| 4,287,155 | 9/1981 | Tersteeg et al. .................... 422/64 |
| 4,318,994 | 3/1982 | Meyer et al. . |
| 4,713,974 | 12/1987 | Stone ................................. 73/864.23 |
| 4,795,710 | 1/1989 | Muszak et al. .................... 435/287 |
| 4,956,148 | 9/1990 | Grandone . |
| 5,077,013 | 12/1991 | Guigan ................................ 422/64 |
| 5,133,936 | 7/1992 | Umetsu et al. ..................... 422/64 |
| 5,192,506 | 3/1993 | Kureshy . |
| 5,200,151 | 4/1993 | Long . |
| 5,207,987 | 5/1993 | Kureshy . |
| 5,246,665 | 9/1993 | Tyranski et al. .................... 422/64 |
| 5,324,481 | 6/1994 | Dunn et al. . |
| 5,340,747 | 8/1994 | Eden . |
| 5,374,395 | 12/1994 | Robinson et al. . |
| 5,424,036 | 6/1995 | Ushikubo ............................ 422/64 |
| 5,456,882 | 10/1995 | Covain ................................ 422/64 |
| 5,518,686 | 5/1996 | Masterson et al. . |
| 5,580,524 | 12/1996 | Forrest et al. . |

(List continued on next page.)

FOREIGN PATENT DOCUMENTS

| | | |
|---|---|---|
| 0802413A2 | 10/1997 | European Pat. Off. . |
| 58-120165 | of 1983 | Japan . |
| 2-7115 | 9/1990 | Japan . |
| 5504627 | 9/1991 | Japan . |
| 9503060 | 3/1995 | Japan . |
| WO0913335 | 9/1991 | WIPO . |

OTHER PUBLICATIONS

European Search Report, EP 98 30 4820, dated Nov. 15, 1999.

*Primary Examiner*—Long V. Le
*Attorney, Agent, or Firm*—McDonnell, Boehnen Hulbert & Berghoff

[57] ABSTRACT

An incubation station has a carousel for receiving a plurality of test sample cards. An even temperature and air flow distribution inside the carousel and incubation of the cards over time at the proper temperature was found to be critically dependent upon air flow characteristics within the incubation station. To optimize air flow, the carousel was given an open rear side that is exposed to an air distribution table having a cover plate placed adjacent to the rear surface of the carousel. The cover plate has a plurality of elongate slots positioned in a symmetrical ring-shaped pattern in registry with the carousel. The elongate slots are positioned at an angle relative to the slots in the carousel such that each carousel slot receives air from more than one slot. An extra fan was also added to the system to increase the flow of air into the air table. Scallop features on the carousel walls also promote even distribution of air flow over the cards. The carousel may be divided into a plurality of carousel segments to increase ease of removal and insertion of the carousel into the incubation station and manufacturability of the carousel.

9 Claims, 25 Drawing Sheets

U.S. PATENT DOCUMENTS

| | | | |
|---|---|---|---|
| 5,595,707 | 1/1997 | Copeland et al. | 422/64 |
| 5,609,828 | 3/1997 | O'Bear . | |
| 5,610,069 | 3/1997 | Clark et al. . | |
| 5,645,800 | 7/1997 | Masterson . | |
| 5,646,049 | 7/1997 | Tayi . | |
| 5,738,827 | 4/1998 | Marquiss | 422/104 |
| 5,762,873 | 6/1998 | Fanning et al. . | |
| 5,863,754 | 1/1999 | Bajard . | |

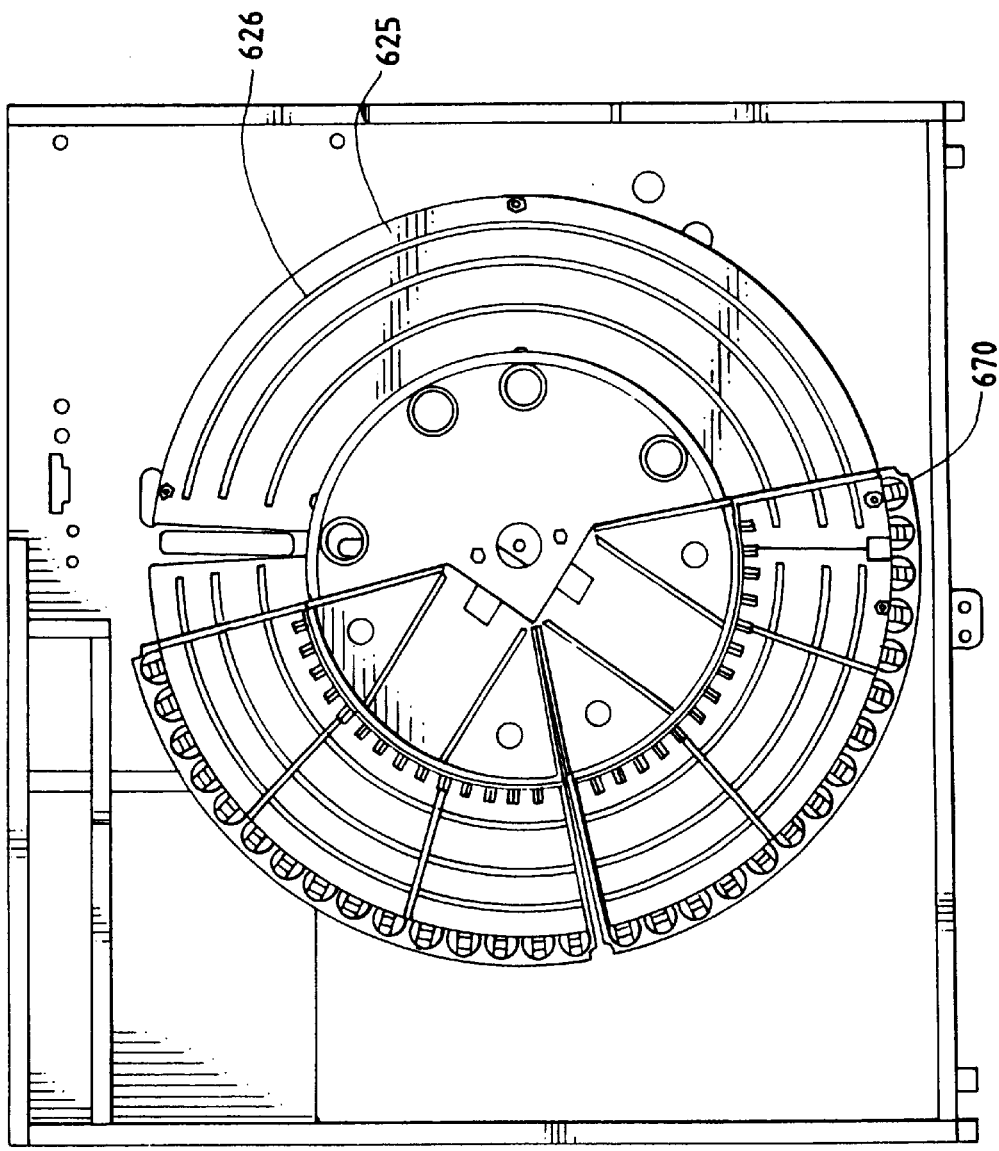

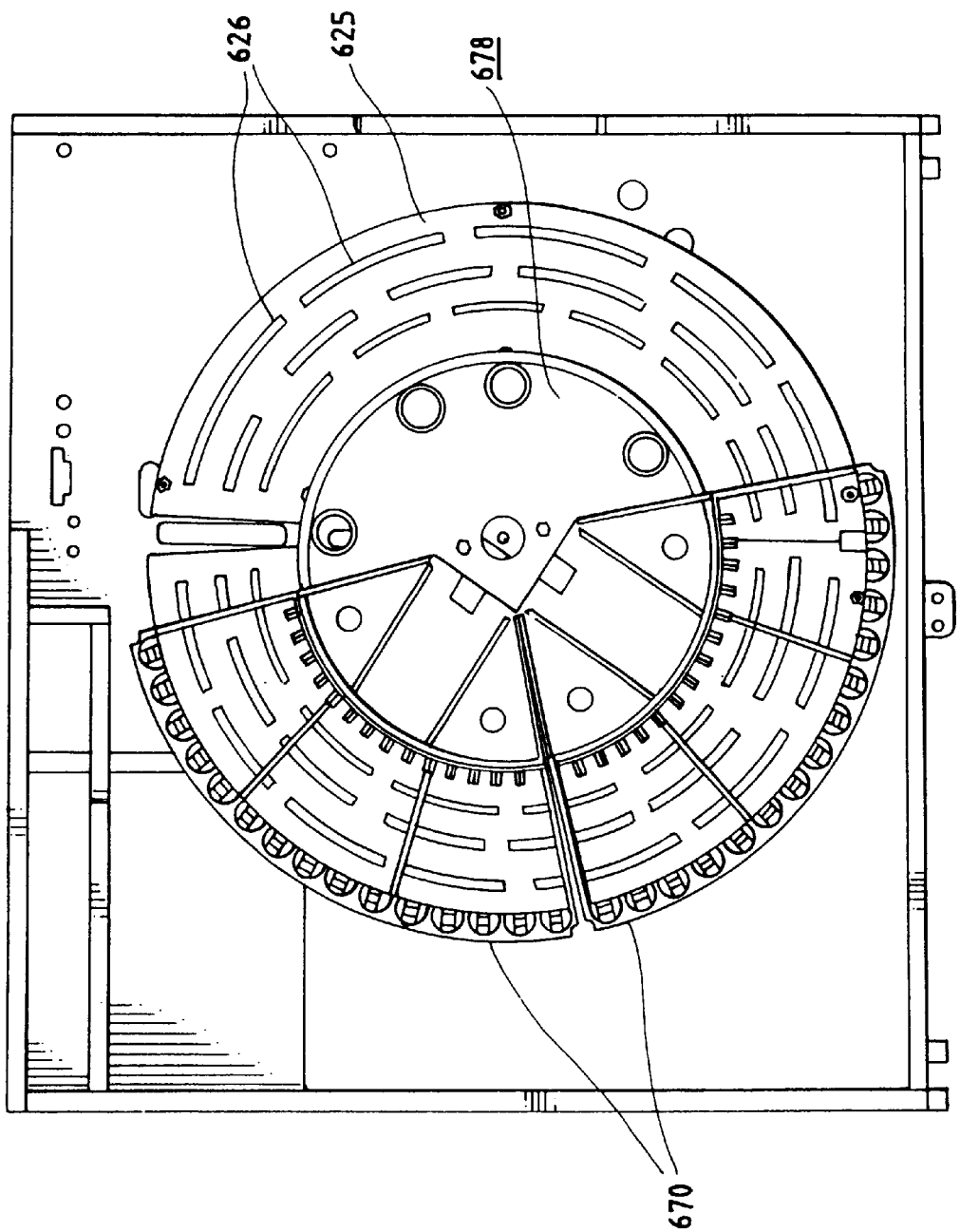

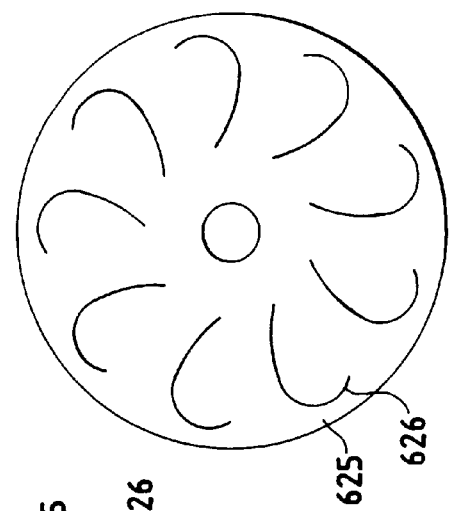
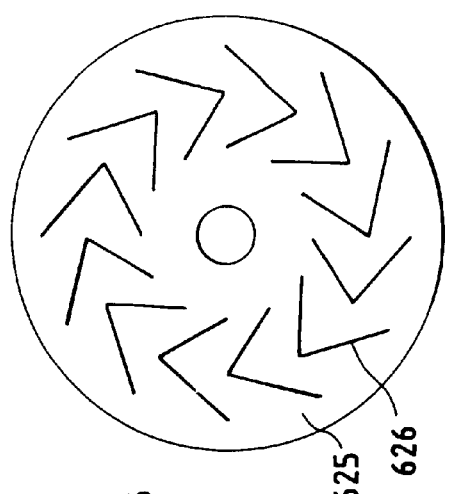
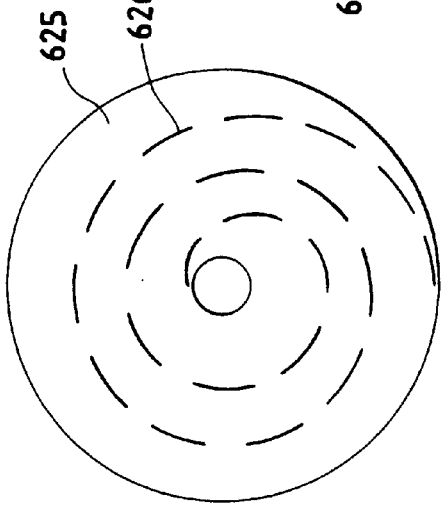
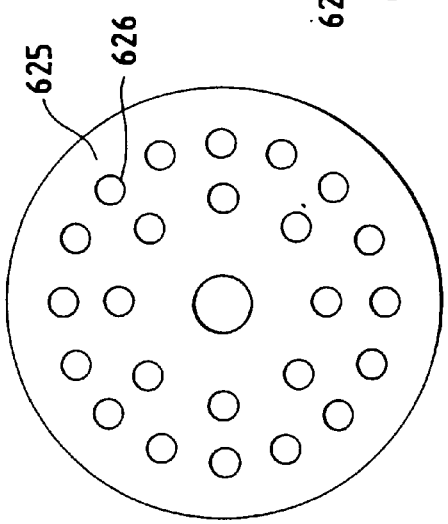
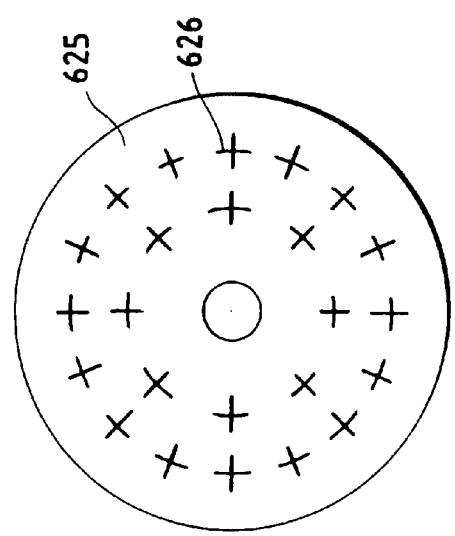
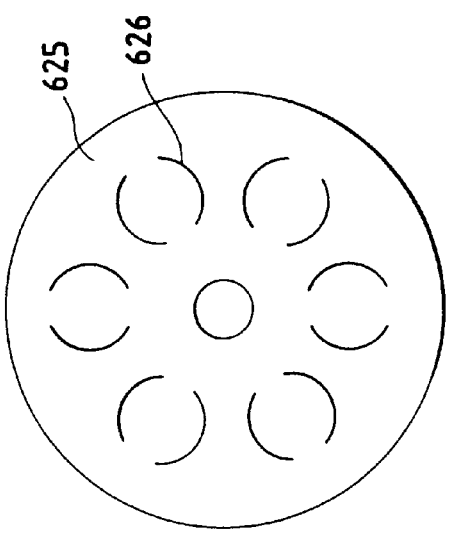

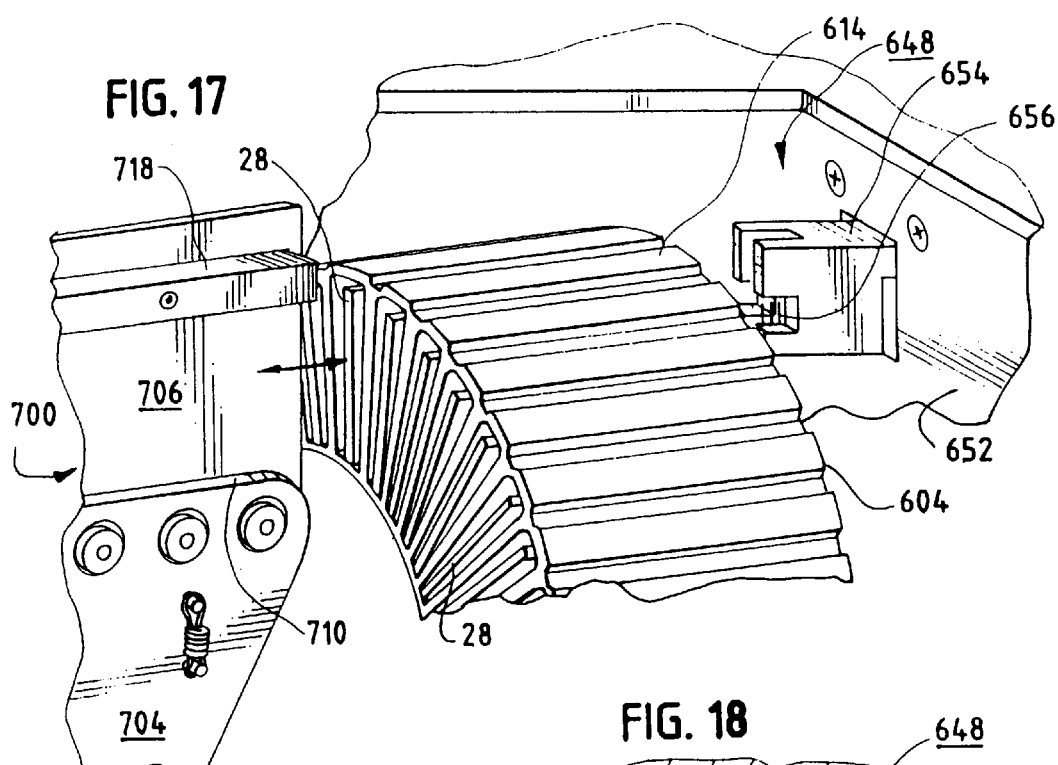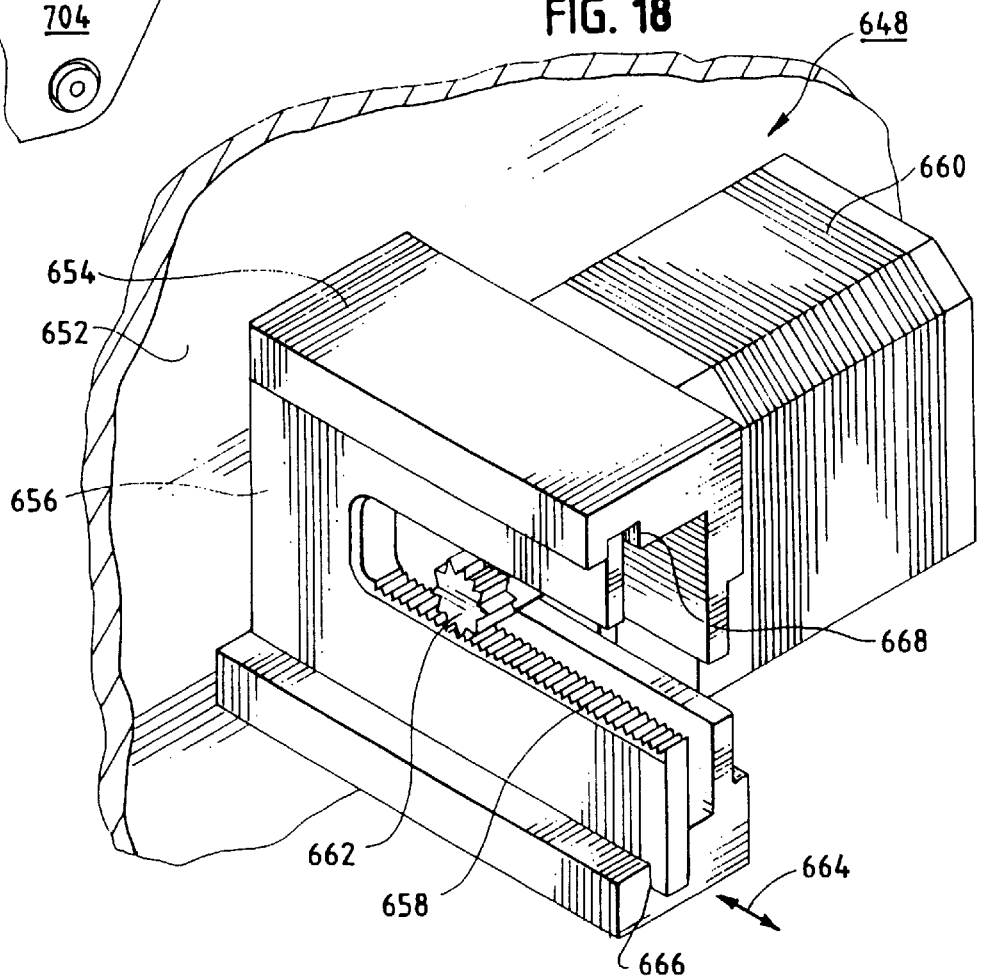

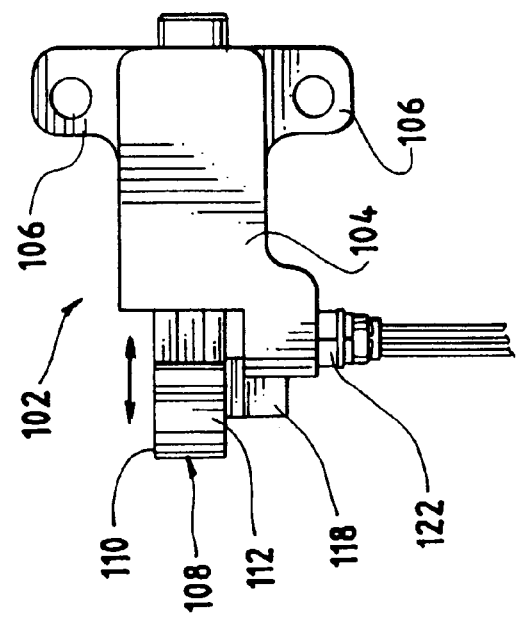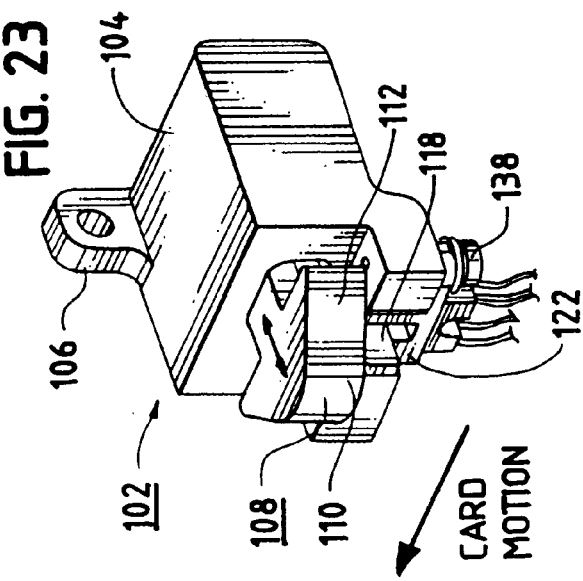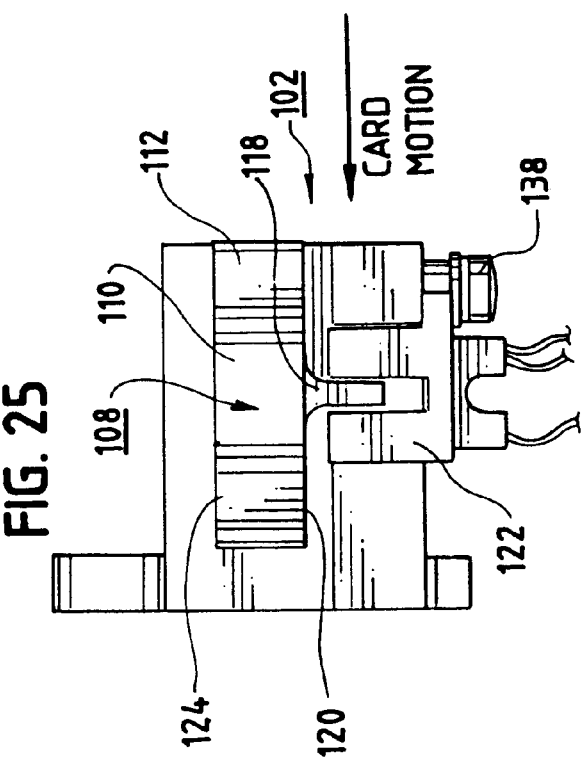

CAROUSEL FOR INCUBATION STATION

CROSS-REFERENCE TO RELATED APPLICATION

This is a division of application Ser. No. 08/905,374, filed Aug. 4, 1997, allowed, which is a continuation in part of application Ser. No. 08/604,672 filed Feb. 21, 1996, now U.S. Pat. No. 5,762,873.

BACKGROUND OF THE INVENTION

A. Field of the Invention

This invention relates generally to the field of analytical instruments for conducting biological sample testing, and more particularly to an incubation station for an analytical instrument that incubates test sample cards or the like. The test sample cards have one or more wells for containing a fluid or test sample containing a microbiological agent (such as a microorganism) and a reagent. The incubation station maintains the test sample card at a predetermined desired temperature (such as 35.5° C.) so as to promote a reaction between the microbiological agent and the reagent.

B. Description of Related Art

A variety of test sample cards are described in the patent literature which have a well or reaction site for receiving a fluid sample containing a microbiological agent, such as a microorganism, and a reagent. Several representative patents include Meyer et al., U.S. Pat. No. 4,318,994, Charles et al., U.S. Pat. No. 4,116,775; Fadler et al., U.S. Pat. No. 4,038,151, O'Bear et al., U.S. Pat. No. 5,609,828 and Charles et al., U.S. Pat. No. 4,118,280. These patents describe a test sample card having a plurality of wells arranged in the test sample card body. The reagent is typically loaded in the wells of the card during the completion of manufacture of the card. The reagent typically comprises a growth medium for the microbiological agent. It is known to load a different reagent in each of the wells of the card in order to perform identification testing of a fluid sample containing an unknown microbiological agent or organism. It is also known to use the cards to test the microbiological agent for susceptibility to antibiotics by loading various antibiotic reagents into the wells.

In the sample testing system described in the Charles et al '280 patent, after the well of the test sample card has been loaded with the fluid sample, the card is incubated for a period of time (typically between 2 and 18 hours at a temperature of approximately 35° C.) so as to promote a reaction between the microorganism and the reagent, i.e., growth of the microorganism. During the incubation period, the well is periodically subject to optical analysis by a transmittance light source and a detector which are positioned on opposite sides of the well, or by alternate detection methods. If the growth medium or reagent is specifically suited for or "matches up" with the particular microorganism in the fluid sample, the population of the microorganism increases substantially, or some other predetermined reaction, i.e., chemical reaction, takes place, which results in the well turning cloudy and thus having a change in light transmission characteristics. The detector determines the amount of light that is transmitted from the source through the well. By comparing the transmittance measurement over a period of time, typically several hours at least, with an initial transmittance measurement, it is possible to determine whether in fact the reagent and microbiological agent are matched by virtue of the change in transmittance measurement reaching a threshold value, such as 25 or 30 percent. The change in light transmission characteristics therefore can be used to indicate the presence of a specific microorganism in the well for purposes of identification or determine its sensitivity to antibiotics. Identification and susceptibility may also be detected by other optical measurements such as fluorescence where a fluorescent agent is provided in the growth medium. These methods could also be useful for other temperature dependent kinetic assays such as analytical chemistry or nucleic acid probe based testing.

Due to the fact that the test sample cards described above are often used in clinical and industrial laboratories to identify unknown microorganisms in human test samples, or food test samples generally for the purpose of diagnosing or detecting disease causing microorganisms, the art has recognized that the time required for incubation of the test sample card should be kept to a minimum, so that results can be obtained as quickly as possible. Further, since multiple cards are typically incubated simultaneously in an analytical instrument, it is important that the incubation station be designed such that all of the cards be maintained at the same incubation conditions for relatively long periods of time. Additionally, the card should be incubated in a manner in which all parts of the card are maintained at the same temperature and air flow, so as to provide an even temperature and oxygen distribution to all the wells in the test sample card.

The incubation and reading station described in the above-reference Charles et al. '280 patent meets these requirements fairly well, and has been commercialized with success by the assignee of the present invention. However, the station is essentially a manual station, in that it requires the test sample cards to be externally prepared and manually loaded into station. As such, this design is not optimal for use in a fully automated analytical instrument in which the cards are prepared (i.e., loaded with the test sample) and introduced into and removed from the incubation station automatically. Achieving the above-described performance criteria for an incubation station in a fully automated analytical instrument is a particularly difficult task.

The present inventors have developed an incubation station for an analytical instrument that is a part of a fully automated system. The station is described in detail herein. In the process of developing the station, they have made several discoveries. First, the physical structures or framework that hold the cards in place in the incubation station can adversely effect the even flow and distribution of warm air introduced into the incubation station. Second, this disruption in the distribution of warm air, caused by the carousel structures can lead to localized pools of warmer and cooler air or variances in air flow across the card, which can adversely affect the even or uniform incubation of the card and prolong the amount of time required to incubate the card sufficient to achieve a test result. Third, the inventors have also discovered that the temperature and/or airflow at various locations in the incubation station are different relative to card position by an amount that is also sufficient to adversely affect the time needed to obtain test results. The inventors have also discovered that the solution to these problems has been to incorporate novel features in the construction of the incubation station that optimizes the flow of warm air over the test sample cards, and that accounts for or is accord with the geometry and spatial distribution of wells in the card and structures that hold the cards in place in the incubation station.

As a result of these findings, the inventors have created a design of a incubation station for a test sample card that is not only particularly well suited for use in an automated analytical instrument, in that it is a fully automatic system, but have also designed the incubation station to achieve a substantially constant temperature distribution and air flow around the test sample cards for as long a period of time as required to incubate the test sample card.

Accordingly, a principle object of the invention is to provide a fully automated incubation station for an analytical instrument for test sample cards that does not require manual loading of the cards into the incubation station.

Another object of the invention is to provide an incubation station for an analytical instrument that provides for even temperature distribution and air flow throughout the incubation station, so as maintain all of the test sample cards at the proper temperature and air flow throughout the incubation period.

Yet another object of the invention is to provide an incubation station for an analytical instrument that maintains the entire test sample card at the proper temperature and air flow and avoids localized differences in air flow or warm or cool sites on the test sample card.

Yet still another object of the invention is to provide an incubation station that is of a relatively compact size and construction, so as to reduce the volume of space required for the incubation station.

Still another object of the invention is to provide a novel air distribution table structure in an incubation station that has an arrangement of openings that promotes the even distribution of air flow over the test sample cards installed in a carousel in the incubation station.

Another object of the invention is to provide a novel carousel structure in which the carousel is divided into discrete segments, and provide a means to remove the carousel segments to promote easy insertion and removal of the segments for cleaning and maintenance.

SUMMARY OF THE INVENTION

An incubation station for a plurality of test sample cards is provided. The incubation station includes a circular carousel having a plurality of slots for receiving the test sample cards. The carousel has a front side portion and an opposite rear side portion. An enclosure is provided for enclosing the carousel and which has at least one opening therein for admitting warm air into the enclosure.

An air distribution plate or airflow table is provided adjacent to the rear side portion of the carousel and in communication with the opening, for directing said warm air over a plurality of card receiving slots in the carousel from the rear side portion of the carousel. In order to improve air flow over the slots of the carousel, the rear side portion of the carousel adjacent to the air distribution plate is substantially open and free of obstructions so as to permit uninterrupted air flow over the test sample cards sufficient to maintain a substantially evenly distributed and substantially constant temperature and air flow over the test sample cards in the carousel. The front side of the carousel is also substantially open so as to allow recirculation of the air.

In a preferred embodiment of the invention, the air distribution plate comprises a first or front surface having a plurality of elongate openings through which the warm air flows towards the carousel. It has been discovered that air flow and even temperature distribution is promoted by arranging the elongate openings in the surface of the air distribution plate in a manner such that each of the elongate openings are oriented at an angle relative to the slots of the carousel, such that the elongate openings overlap at least two of the slots of the carousel. In this manner, each of the test sample cards in the slots receives warm air from at least two elongate openings in the air distribution plate. A preferred embodiment of this arrangement comprises the arrangement of the elongate openings in a symmetrical, ring-shaped pattern in substantial registry with the rear side portion of the carousel. Other alternative openings designs are also envisioned, such as a plurality of concentric rings, or alternatively, arcuate sections, formed in the air distribution plate.

Another feature of the invention is that the carousel may be constructed in a plurality of discrete, separable carousel segments, for example, four pie-shaped segments each forming approximately 90 degrees of an arc. Each of the segments are mounted together in the enclosure to a mounting plate to form a circular carousel, but are separately removable from the enclosure. This feature promotes an easier manufacturing and insertion and removal of the carousel from the enclosure for cleaning and maintenance. Recessing the front surface of the carousel also promotes even flow of the return air.

In this embodiment of the invention, it has been discovered that air flow over the cards within discrete, separable carousel segments is achieved by forming the rear side surface of the segment with a substantial void so as to improve air flow from the air distribution plate over the test sample cards. Scallop or other void features provided on the end walls of the segments also assist is providing sufficient air flow over the test sample cards and promotes efficient recirculation of the air.

These and still other objects, advantages, and features of the invention are described below in the following detailed description of presently preferred embodiments of the invention.

BRIEF DESCRIPTION OF THE DRAWINGS

A presently preferred embodiment of the invention is described below in conjunction with the appended drawing figures, wherein like reference numerals refer to like elements in the various views, and in which:

FIGS. 12A–12H depict other possible arrangement of openings in the air distribution cover plate that should promote good air flow over the carousel and test sample cards contained therein;

FIG. 17 is a perspective view of a push mechanism located at the top of the bulkhead of FIG. 6 that pushes the cards out of the slots in the carousel of FIG. 2 into the sample card transport system of FIG. 1;

FIG. 18 is a perspective view of the push mechanism as seen from the rear of the bulkhead;

FIG. 23 is a perspective view of a card separation and detection device that is a preferred alternative to the card separation mechanism illustrated in FIG. 3;

FIG. 24 is a side elevational view of the alternative card separation and detection device of FIG. 23;

FIG. 25 is a front elevation view of the alternative card separation and detection device;

FIG. 26 is an exploded perspective view of the alternative card separation and detection device;

FIG. 27 is a side view of the alternative card separation and detection device, partially in section, showing the position of the threaded shoulder screw within the body of the housing, and the flag on the actuator relative to the optical sensor; and FIG. 28 is a bottom plan view of the alternative card separation and detection device, partially in section, showing the position of the shoulder screw within the body of the housing.

DETAILED DESCRIPTION OF THE PREFERRED EMBODIMENT

Overview of Preferred Automatic Sample Testing Machine

The preferred embodiment of the inventive incubation station will be described in conjunction with a presently preferred fully automated biological sample testing instrument for test sample cards. It will be appreciated, however, the invention is not limited to the particular automated biological sample testing instrument illustrated, as the incubation station could be used with other machine designs, test methodologies such as analytical chemistry or nucleic acid probe based assays, and can even be used in a less fully automated machine or even a manual system.

Figure 1:
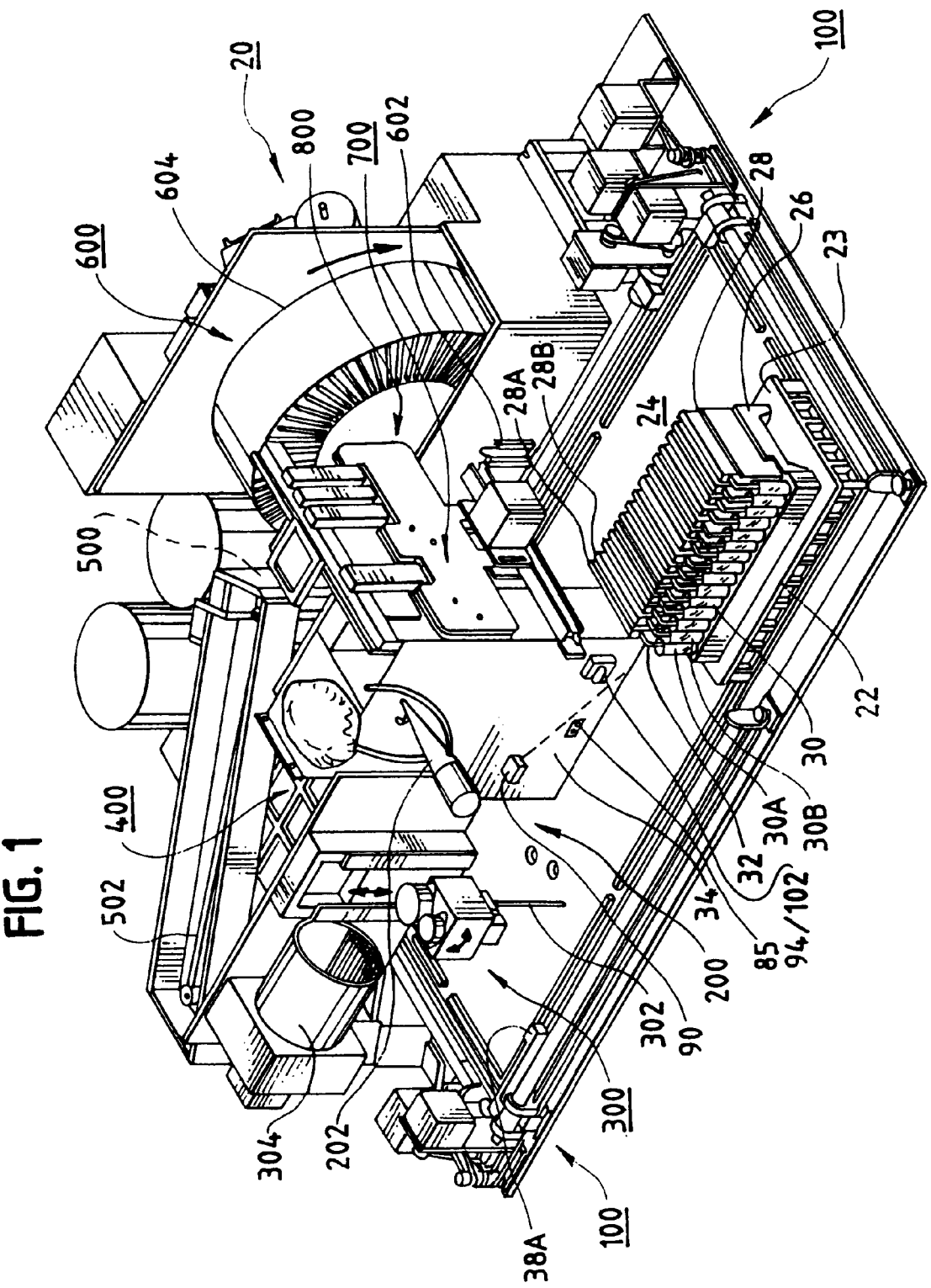
FIG. 1 is a perspective view of a preferred automatic biological sample testing instrument that incorporates the incubation station in accordance with the invention. The card disposal station and cover panels for the instrument are removed in order to more clearly show the other features of the machine.
Figure 1A:
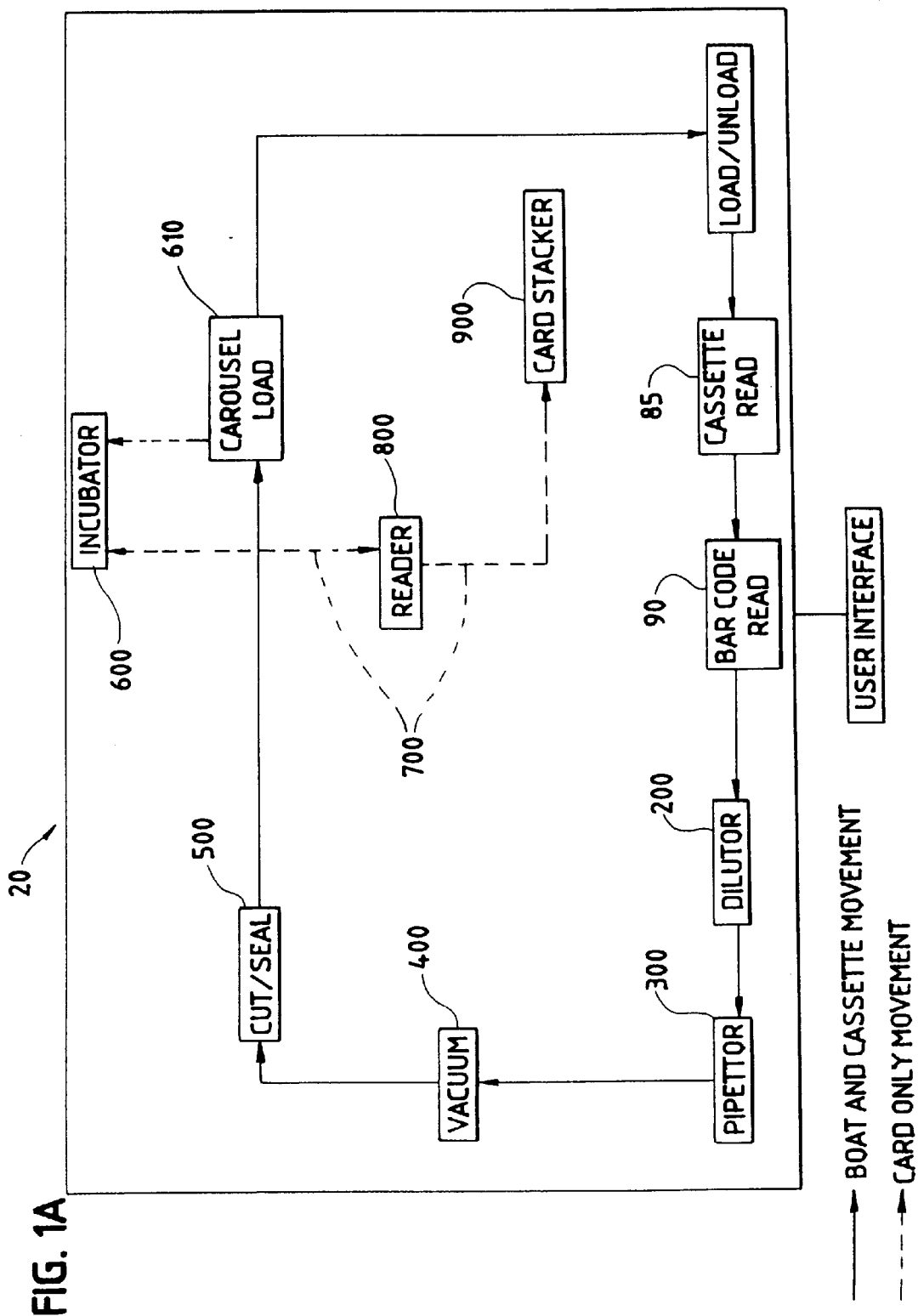
FIG. 1A is a block diagram of the all of the principal stations in the instrument of FIG. 1.
Figure 2:
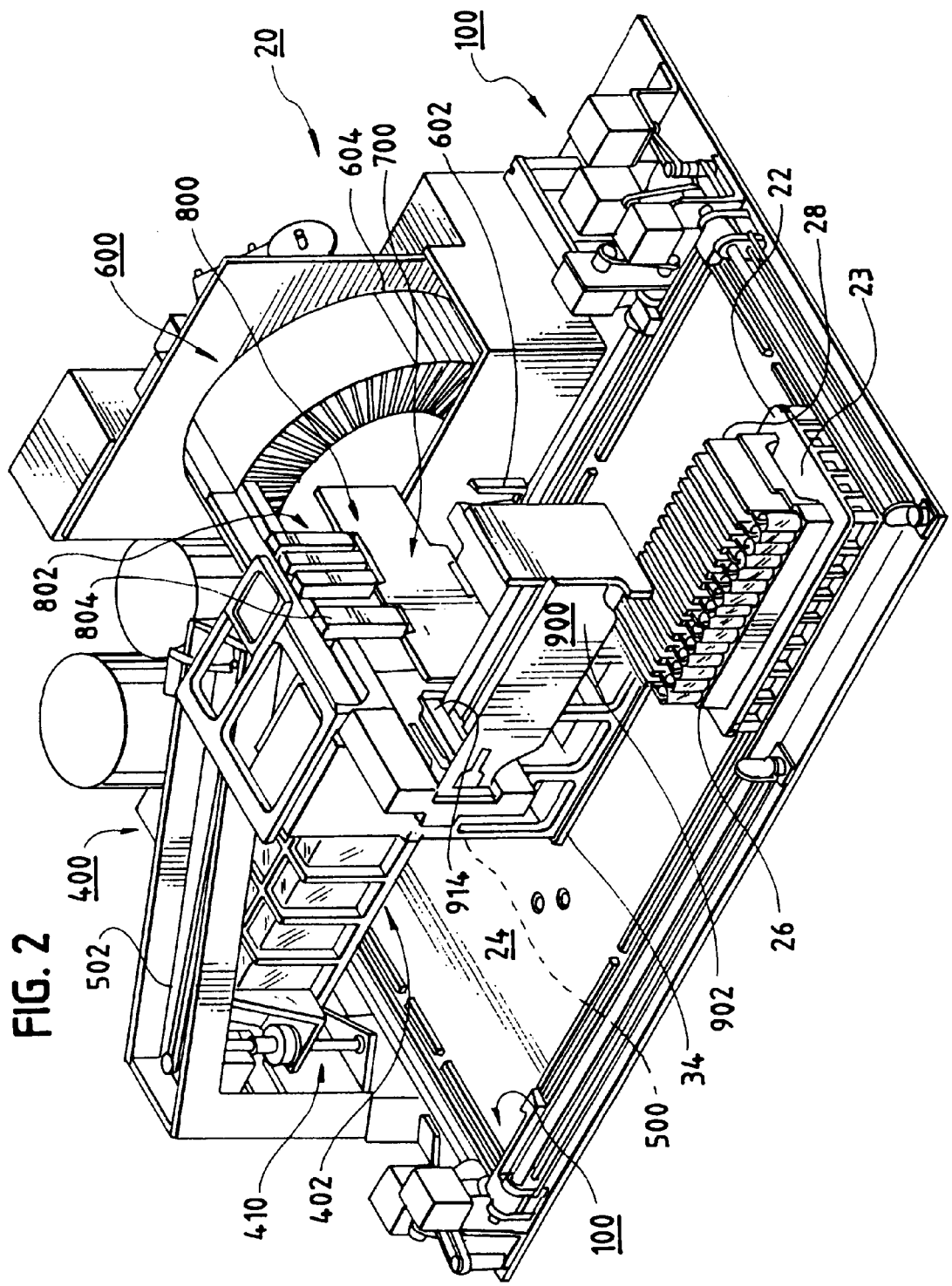
FIG. 2 is a perspective view of the instrument of FIG. 1, with the diluting and pipetting stations removed to better illustrate the vacuum station, and with the stacking disposal station included to show its relationship to the sample card transport and optical systems.
Figure 3:
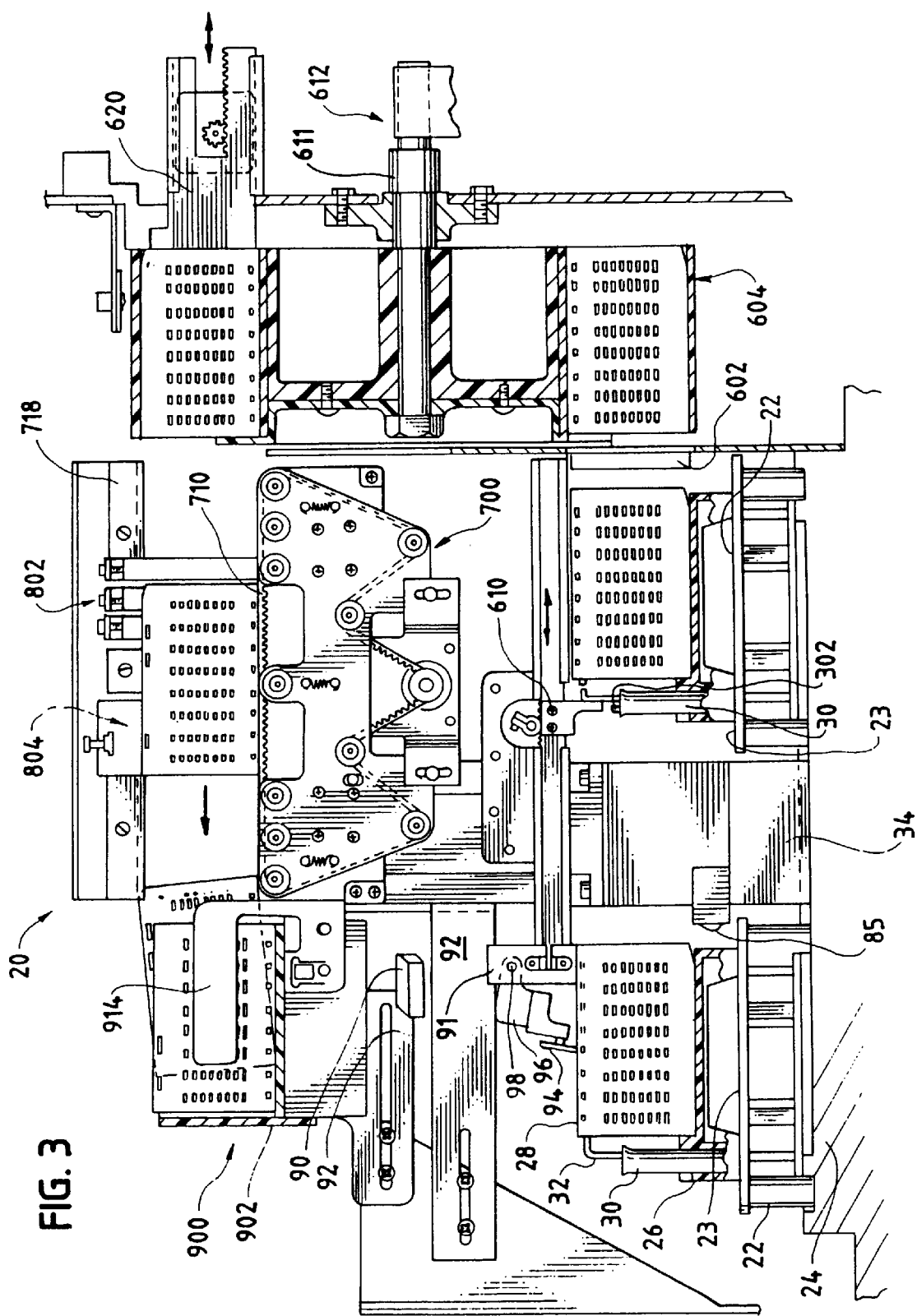
FIG. 3 is an end view of the instrument, partially in section, as seen from the right-hand side of the instrument in FIG. 1 looking toward the center mount, showing, among other things, a mechanism for loading the test sample cards into the carousel and a mechanism for separating the cards within the cassette to better enable a bar code positioned at the top of the card to be read by an optical reader.

FIG. 1 is a perspective view of a biological sample testing machine or instrument 20 that conducts analysis of test sample filled cards 28 according to a preferred embodiment of the invention. The instrument 20 has a set of removable cover panels covering the machine and presenting an aesthetically pleasing appearance and allowing user access to system components, that are not shown, in order to better illustrate the functional aspects of the machine. In FIG. 1, a stacking card disposal station for the cards 28 has been removed in order to illustrate the other components of the instrument. The card disposal station 900 is shown in FIG. 2. FIG. 3 is an end view of the machine, partially in section, showing the position of the test sample cards 28 as they are processed in several of the stations in the machine 20. FIG. 1A is a block diagram of the machine 20 as a whole, showing the layout of the stations and the path of a boat and cassette assembly and test sample cards through the machine in a preferred embodiment of the invention.

Referring now primarily to FIGS. 1, 1A, 2 and 3. The biological sample testing machine 20 includes a biological test sample positioning system 100, consisting of four independent motor-driven paddles, which pulls a sample tray 22 (referred to herein as a "boat") incorporating a cassette 26 across a base pan 24 around the machine 20 to several discrete stations, where various operations are performed on the cards and receptacles in the cassette 26. The cassette 26 consists of a holder that fits snugly into the boat 22 having a plurality of slots for receiving the test sample cards 28, with each of the slots having enough fore and aft separation distance so as to permit the cards 28 to be rocked slightly, in the manner described below, as the cassette 26 and boat 22 are moved past the bar code reading station 90 in the machine.

Prior to the start of the procedure, a technician loads a cassette 26 with a plurality of test cards 28 and receptacles such as test tubes 30 containing biological or control samples to be tested. Each test card 28 has an L-shaped transfer tube 32 protruding therefrom for permitting the fluids containing biological samples to be drawn from the test tubes 30 into the reagent-filled wells of the test cards 28. The technician places the loaded cassette 26 into the boat 22 at a loading station for the machine, such as the front, right hand corner of the base pan 24 shown in FIG. 1. The combined boat 22 and loaded cassette 26 are then automatically moved as a unit over the surface of the base pan 24 about the machine 20 by the test sample positioning system 100.

In a typical microbiological testing scenario, described below for purposes of illustration but not limitation, the test cards 28 come in two varieties: (1) identification cards, in which particular different growth media are placed in each of the wells of the card 28 when the cards are manufactured, and (2) susceptibility cards, in which different concentrations of different antibiotics are also placed in each of the wells of the card 28. The identification cards are used to identify the particular unknown biological agent, i.e., microorganism, present in the sample. The susceptibility cards are used to determine the susceptibility of the biological agent to various concentrations of antibiotics or other drugs. In the test procedure described below, identification and susceptibility tests can be performed on a single sample in one cycle of operation of the machine 20 (i.e., one test run). To accomplish this, the cassette 26 is loaded such that a test tube 30A containing a biological sample, connected via a transfer tube 32 to an identification card 28A, is placed adjacent to an empty test tube 30B connected via a transfer tube 32 to a susceptibility card 28B.

The cards 28 preferably contain bar codes as well as other identifying indicia on the upper portion of the card for reading by a bar code reader 90 (FIG. 3) built into the machine 20. The bar codes are unique to each card, and identify card information such as card type, expiration date, and serial number, and are used to correlate test data and/or results from the cards with the patient and the biological sample. In addition, the entire boat or cassette may have sample information for all of the cards loaded in the cassette stored on one or more memory devices affixed to the cassette 26, such as a memory button or "touch button" available from Dallas Semiconductor Corp., 4401 S. Beltwood Parkway, Dallas Tex. A card identification reading station, including a card separation device for promoting reading of the cards, is described in detail below.

In the representative example shown in FIG. 1, seven or eight of the test tubes 30 in the boat 22 contain biological samples, and are in fluid communication with identification cards 28A by the straw-like transfer tube 32. The biological sample test tube 30A and its associated identification card 28A can be thought of as a set. The biological sample test tubes and identification cards are typically arranged in an alternating pattern in the cassette 26. Each biological sample test tube 30A and identification card 28A set is adjacent to an empty test tube 30B placed in communication with a susceptibility card 28B via a transfer tube 32. It will be appreciated that the cards and associated test tubes could be ordered in any order in the cassette 26 depending on the particular testing requirements for the samples. For example, the cards could be arranged as follows: identification (ID), susceptibility (SU), ID, ID, ID, SU, SU, ID, SU . . . . Further examples would be all identification cards and all susceptibility cards.

The test sample positioning system 100 operates to move the boat 22 and cassette 26 over the base pan 24 to the bar code reading and card detection station 90, described below, and then to a diluting station 200. The diluting station contains a rotating shot tube 202, by which a predetermined volume of diluent (such as saline solution) is added to the empty susceptibility test tubes in the cassette 26, e.g. test tube 30B. Other types of fluids may be added to the test tubes by a rotating shot tube, such as reagents or growth media, thus diluting station 200 is not limited to just adding a diluent to the test tubes. As the leading edge of the boat 22 is moved to the left during this process, it passes under a pipetting station 300. The pipetting station 300 includes a mechanism that automatically removes a pipette 302 from a source of pipettes 304, lowers the pipette 302 into the biological sample test tube 30A, and removes with vacuum a predetermined volume of biological fluid from the biological sample test tube 30A using the pipette 302.

The test sample positioning system 100 then moves the boat 22 to the left by an amount equal to the separation distance between adjacent test tubes 30A and 30B, e.g. 15 mm. The pipetting station 300 then lowers the pipette 302 containing the biological fluid from the biological sample test tube 30A into the adjacent susceptibility test tube 30B (having already received a quantity of diluent from the diluting station 200), expels the fluid into the test tube 30B, mixes the fluid in the test tube 30B and drops the pipette 302 into the susceptibility test tube 30B. The process of movement of the boat 22 by the test sample positioning system 100, adding diluent to the susceptibility test tubes 30B at the diluting station 200, and transferring of biological samples from the biological sample test tubes 30A to the adjacent susceptibility test tubes 30B at the pipetting station 300, continues until all of the identification and/or susceptibility test tubes sets (if any) in the boat 22 have been so processed. By virtue of the close spacing of the pipetting station 300 and the diluting station 200, simultaneous diluting and pipetting operations can be performed on multiple test tubes in a single boat 22. After the last pipetting operation has been performed, the test sample positioning system 100 then moves the boat 22 all the way to the left-hand edge of the base pan 24.

It will be understood by persons skilled in the art that the cassette 26 may be loaded entirely with biological samples in the test tubes 30 and identification cards 28, such as the case where a batch of biological samples are to be tested to identify the contents of the samples. In this example, the diluting and pipetting operations are not necessary. However, in other types of sample testing, growth media, other diluents or reagents or fluids may be added to or withdrawn from the test tubes. In the example of where no diluting or pipetting operations are performed (e.g., where the pipetting and diluting operations were performed off-line), the cassette 26 is loaded with test tubes and cards, and the positioning system 100 would simply move the boat 22 and loaded cassette 26 directly past the diluting station 200 and the pipetting station 300 without stopping, all the way to the left hand edge of the base pan 24.

Once at the left hand edge of the base pan 24, the test sample positioning system 100 operates to move the boat 22 along the left hand edge to a vacuum station 400. The vacuum station 400 is seen better in FIG. 2, which is a perspective view of the machine 20 with the diluting station 200 and the pipetting station 300 removed, and in FIGS. 4 and 5. At the vacuum station 400, a vacuum chamber 402 is lowered onto the boat 22 such that the bottom surface of the vacuum chamber 402 sealingly engages the top peripheral surface 23 of the boat 22. The vacuum chamber has tubing 406, 408 (FIG. 4) that are in communication with a conventional vacuum source for the machine (not shown in FIG. 4). Vacuum is applied to the chamber 402 under microprocessor control, causing air in the interior of the test sample cards 28 to evacuate out of their associated test tubes and to be withdrawn from the chamber 402. The vacuum cycle is precisely managed to optimize filling by using a closed loop servo system to regulate the rate of change of vacuum and the timing of the complete vacuum cycle. After a predetermined period, the chamber 402 is vented to atmosphere under microprocessor control. The venting of the cards causes the fluid in the test tubes 30 to be drawn into the cards 28, filling the wells in the cards 28. After the chamber 402 is vented, the chamber is raised up by a vacuum chamber drive mechanism 410 so as to permit the boat to be moved to the other stations of the machine 20.

Figure 4:
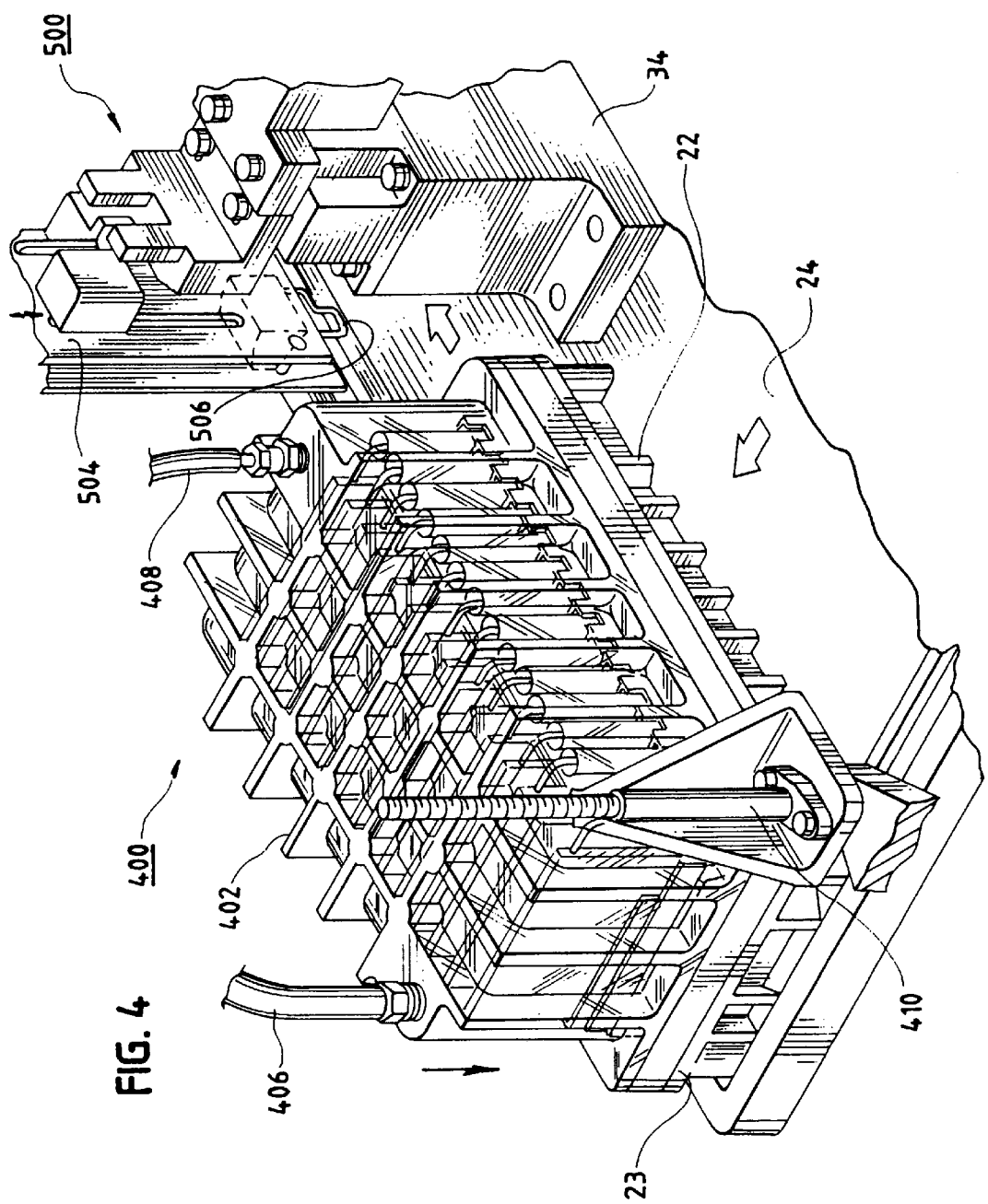
FIG. 4 is a detailed perspective view of the vacuum chamber of the vacuum station of FIG. 2 engaging the top surface of the boat, as it would be when the fluid samples are loaded into the cards.
Figure 5:
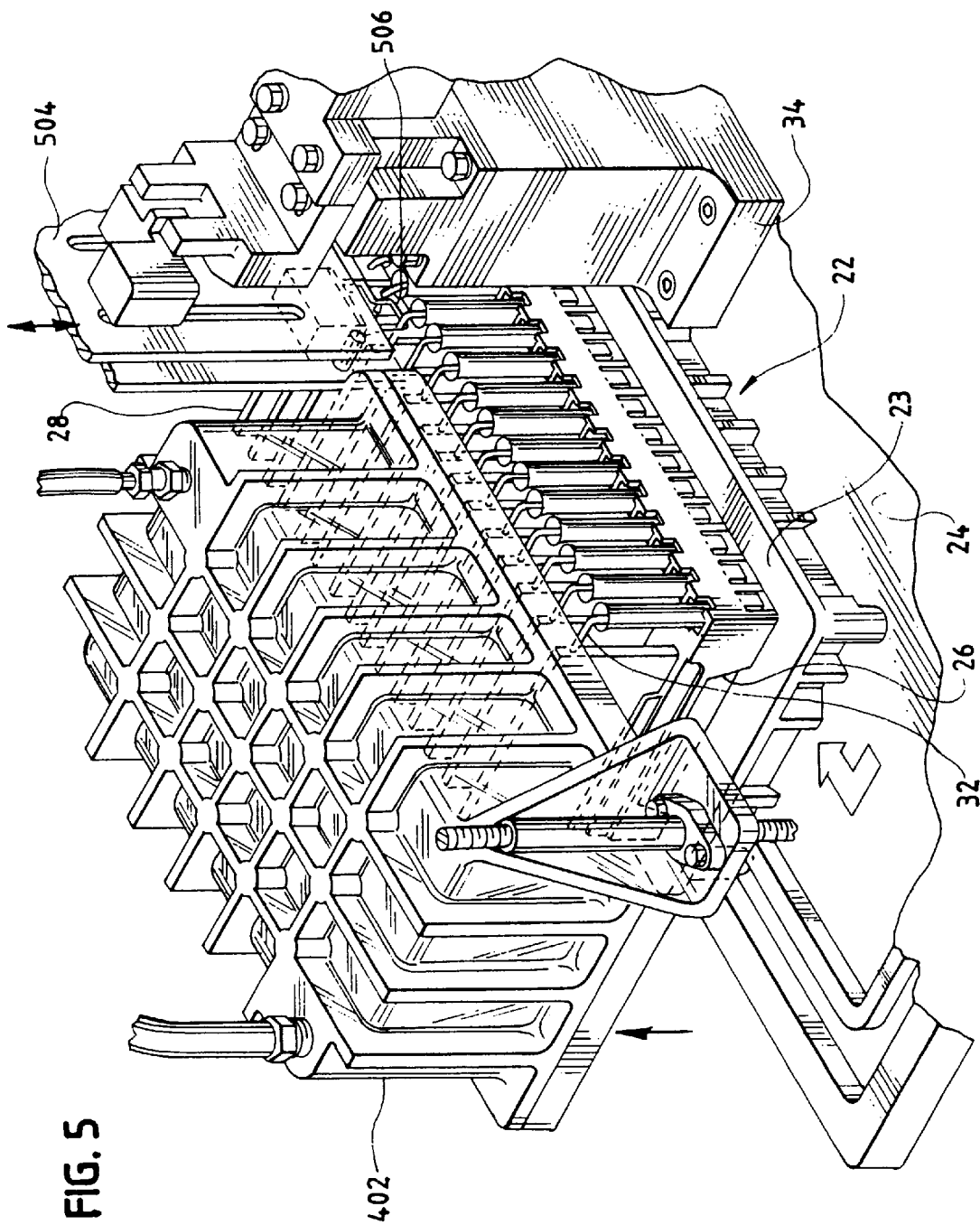
FIG. 5 is a detailed perspective view of the cut and seal station, showing the hot cutting wire cutting through the transfer tubes for the cards when the boat is advanced past the hot cutting wire, thereby sealing the interior of the cards.

The test sample positioning system 100 then operates to advance the boat 22 to the right across the rear of the base pan 24 to a cut and seal station 500, located behind the center mount 34 in FIGS. 1 and 2. Referring to FIGS. 4 and 5, the cut and seal station 500 consists of a hot cutting wire 506 and attached support plate 504, and a drive mechanism 502 (e.g., stepper motor, drive belt and lead screw) that lowers the cutting wire and support plate 504 to the same elevation as the top portion of the transfer tubes 32 adjacent to where the transfer tubes 32 enter the test cards 28. As the boat 22 is advanced past the cut and seal station 500, the transfer tubes 32 are forced past the hot cutting wire 506. By virtue of the assistance of fore and aft constraints placed on the movement of the cards 28 by the walls of the cassette 26, and the lateral constraints on the movement of the card 28 by the cassette and wall structures of the machine 20, the hot cutting wire cuts the transfer tubes 32 by melting of the transfer tube material as the boat 22 is slowly advanced past the hot cutting wire 506. A small stub of transfer tube material is left on the exterior of the card 28. The stub seals the interior of the card 28 from the atmosphere (except, in certain types of cards, for possible diffusion of gasses such as oxygen through oxygen permeable tape covering the sample wells). When the boat is advanced past the station 500, the wire 506 is raised up to its upper position.

Referring to FIGS. 1 and 3, the test sample positioning system 100 then advances the boat 22 across the rear of the base pan 24 behind the center mount 34 to the inventive carousel incubation station 600. A reciprocating rack and pinion driver 610 is mounted to the center mount 34 opposite a slot 602 in the machine that pushes the cards off the cassette 26 one at a time through the slot 602 into a vertically oriented carousel 604. The carousel 604 is housed in an enclosure that is maintained at an appropriate incubation temperature. The enclosure is partially removed in FIGS. 1 and 2 in order to show the carousel 604. The carousel 604 is rotated by a drive system 612 in synchronism with the movement of the boat 22 over the rear of the base pan 24 by the test sample positioning system 100, so as to place the next slot in the carousel 604 in line with the slot 602 opposite the next card in the cassette 26. If the carousel is only going to be partially loaded with cards, the operating system of the machine may control the carousel 604 rotation to load the cards into non-adjacent adjacent slots to equally distribute the cards in the carousel in order to balance out the weight distribution in the carousel 604. For example, where the carousel has 60 slots and only 30 cards are to be processed, the cards could be loaded into every other carousel slot.

Additional incubation capacity required for processing a larger number of cards at one time can be provided by using a larger carousel, adding an additional incubation station(s) to the base pan, and adjusting the dimension of the base pan and drive system components as necessary. Additional optics stations may be provided for additional carousels. For example, if the carousel 604 has sixty slots and each cassette holds 15 cards, four full cassettes 26 (FIG. 1) can be processed at once. If a second carousel is added, up to 120 cards could be processed at once. Of course, different capacities could be provided for the cassette 26 and the carousel 604.

After all of the cards 28 have been loaded into the slots of the carousel 604, the boat 22 is advanced along the right hand edge of the base pan 24 back to its starting position (shown in FIGS. 1 and 2) or to an exit position for removal of the cassette 26 (containing, the test tubes, pipettes 302, if any, and transfer tubes remnants) and receipt of a new cassette. Alternatively, the boat 22 could be moved to an exit station located, for example, in the rear or right hand side of the base pan 24.

As the cards 28 are being incubated in the incubation station 600, the cards are periodically, sequentially pushed out of the slots of the carousel 604 at the top of the carousel 604, one at a time, by a reciprocating rack and pinion driver 620 and an associated stepper motor. The cards 28 are moved by an optical scanner card transport station 700 past a fluorescence and/or transmittance optics station 800 having a transmittance substation 802 and/or a fluorescence substation 804. The wells of the card 28 are selectively subject to sets of transmittance and/or fluorescence optical testing according to the analysis needed to be performed by the transmittance and fluorescence optics station 800. The transmittance and fluorescence optics station 800 includes detectors and processing circuitry to generate transmittance and fluorescence data for the wells in the cards 28, and to report the data to a central processing unit for the machine 20. If the test is not complete, the transport station 700 moves the card 28 back into its slot in the carousel 604 for more incubation and additional reading.

Typically, each test sample card will be ejected into the transport station 700 for reading every 15 minutes as the carousel makes one revolution. The rate of rotation could be faster or slower, of course. Typical incubation times for the cards 28 are on the order of one to eighteen hours, consisting of roughly four transmittance and/or fluorescence data sets per hour, each data set consisting of multiple readings, for each of the wells in the card 28 subject to the optical analysis requirements.

After the testing is complete, the cards are moved by the optical scanner transport system 700 into a card output station 900 shown in FIG. 2 and FIG. 3. The card output station 900 consists of a detachable tray or magazine 902 and associated support structure that is positioned to the side of the optical station 800 at approximately the same elevation as the optical station 800. The station 900 has a pressure slide 914 that is moveable within the magazine 902 and a constant force spring biasing the pressure slide towards the front of the magazine. The cards are stacked in the magazine between the pressure slide 914 and oppositely opposed resilient snap elements integrally formed in the sides of the magazine 902. The technician removes the magazine 902 from the machine 20 as needed or when the magazine is full of cards, empties the cards into a suitable biohazard disposal unit, and replaces the magazine 902 back into the machine 20.

Incubation Station Operational Features

Figure 6:
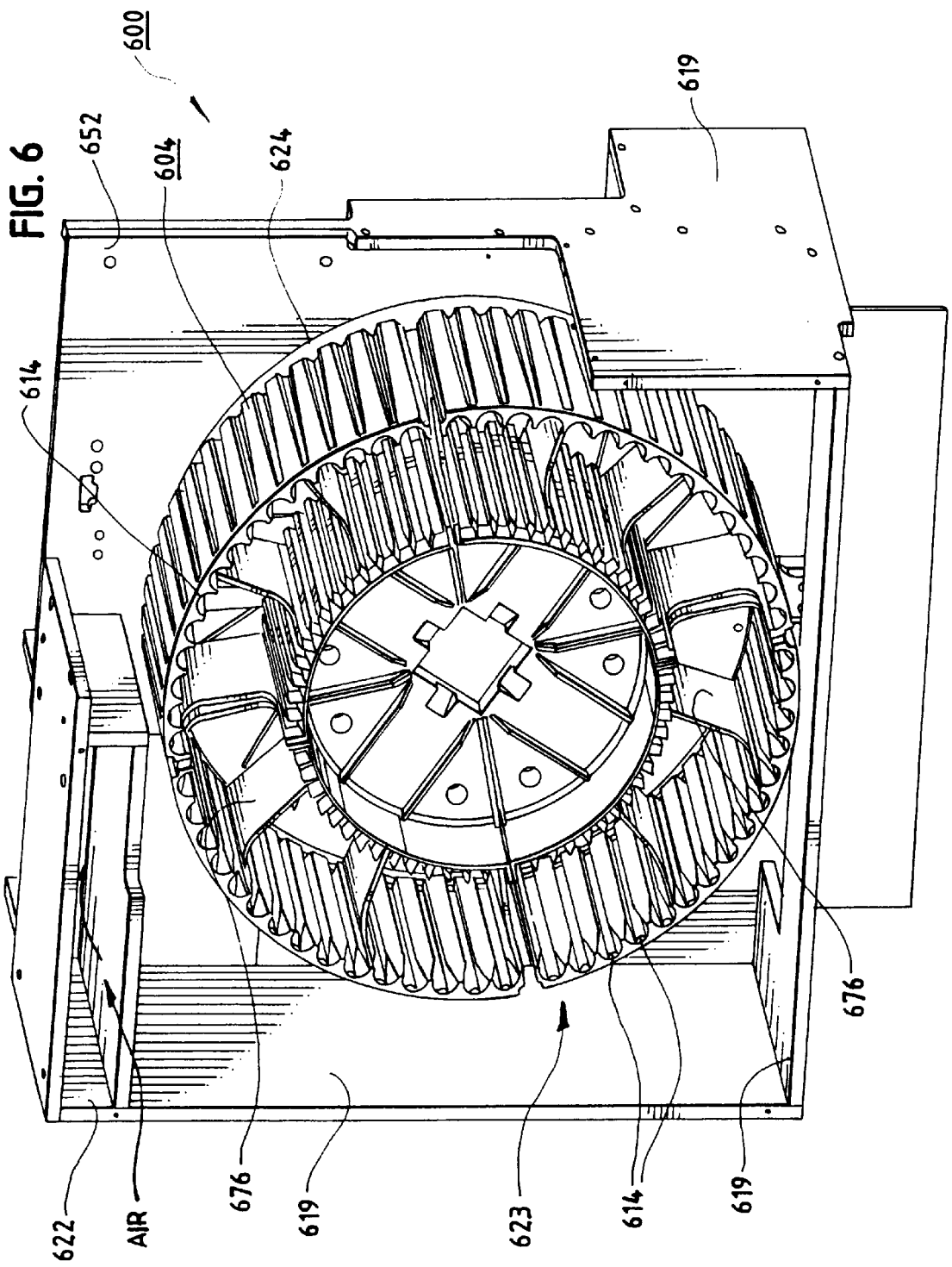
FIG. 6 is a front perspective view of the carousel of FIG. 1 installed in the incubation station, with several of the cover panels of the incubation station removed in order to illustrate the carousel.

FIG. 6 is a front perspective view of the carousel 604 and incubation station 600 of FIG. 1, with several of the cover panels 619 of the incubation station removed in order to better illustrate the carousel 604. The cover panels 619 form an enclosure for the carousel 604 and isolate the carousel 604 from ambient conditions.

The carousel 604 is vertically mounted and rotates about a horizontal axis. An air duct 622 is provided on the upper portion of the station 600 to allow air to circulate from the front portion of the incubation station (containing the carousel 604) to the rear of the station behind the bulkhead 652. A small hole is placed in the rear cover panel parallel to and positioned behind the bulkhead 652 to allow a controlled amount of ambient air into the station. The duct 622 includes an aperture in the bulkhead 652 to allow air to flow down the rear side of the bulkhead between the bulkhead and the rear cover panel, where it is blown over a heater which heats the air, and blown by a second fan 639 (FIG. 9) into an air distribution table 624 positioned behind the carousel 604, in the manner described in detail below.

The carousel 604 has a plurality of slots 614 for receiving the test sample cards. The carousel has a substantially open front side portion 623 through which the cards are introduced into the slots 614 at the lowermost portion of the carousel (see FIG. 3), and an opposite rear side portion facing the air table 624 and the bulkhead 652.

Figure 7:
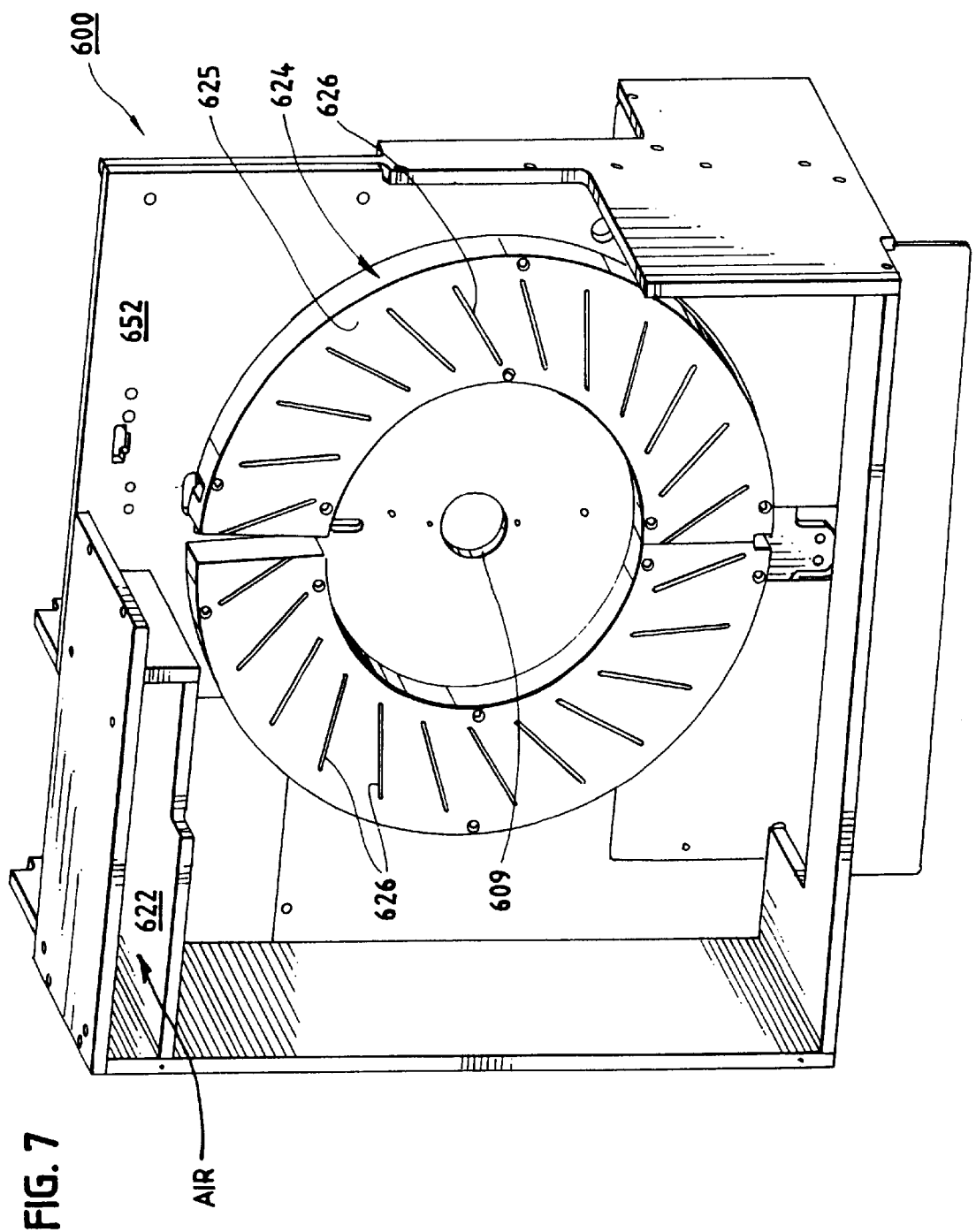
FIG. 7 is a perspective view of the incubation station of FIG. 6 with the carousel, drive shaft and mounting plate removed, in order to better illustrate the air distribution table and cover plate features of the incubation station.

FIG. 7 is a perspective view of the incubation station of FIG. 6 with the carousel 604 removed, in order to better illustrate the air table 624 and air distribution cover plate 625 features of the incubation station. The air table 624 receives warm air from a heater and fan assembly behind the bulkhead 652. The air table 624 has an air distribution cover plate 625 that encloses the air table 624 which is positioned in registry with the slots 614 of the carousel 604. The cover plate 625 has a plurality of elongate openings 626 formed therein that direct the warmed air over the rear side portion of the carousel and over the cards in the carousel slots. In order to promote adequate air flow over the cards, the rear side portion of the carousel adjacent to and opposite the air distribution cover plate 625 is substantially open and free of obstructions so as to permit substantially uninterrupted air flow over the test sample cards. Thin reinforcing ribs connecting the inner and outer circular carousel walls may be provided for strength and molding purposes, but such ribs should be sized so as to occupy a small as possible a surface area in the rear side portion of the carousel. The front portion of the carousel 604 is also spaced from the front cover panel (not shown) of the incubation station and made substantially open and free of obstructions, as shown, so as to promote the efficient recirculation of the air.

Figure 12:
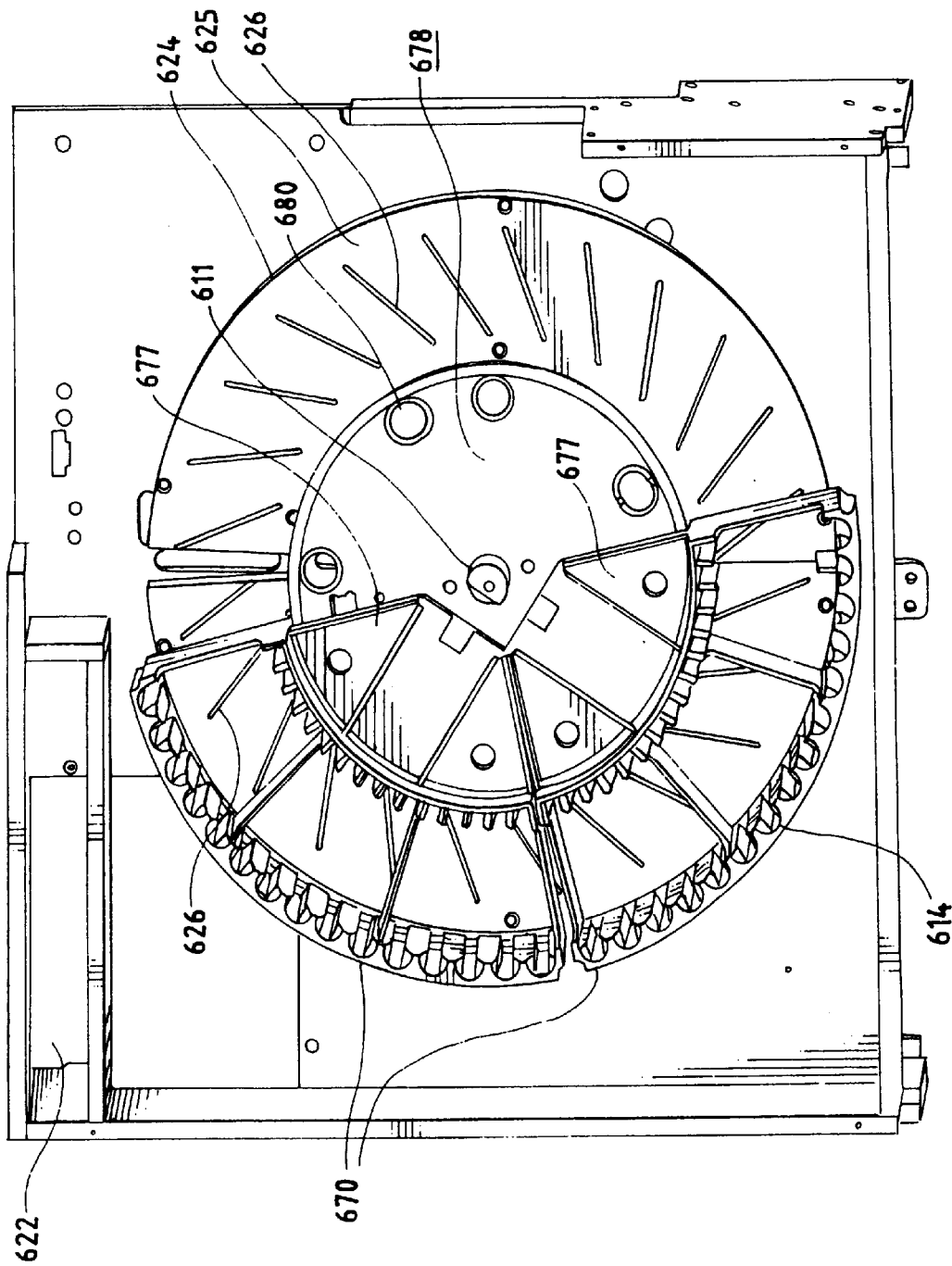
FIG. 12 is a perspective view of two sections of the carousel positioned over the air table, showing the relationship of the elongate openings in the air distribution cover plate of the air table with respect to the card-receiving slots in the carousel.

Referring to FIGS. 6, 7 and 12, it has been found that the size and arrangement of openings 626 in the air distribution cover plate 625 is important to promoting the optimal air flow over the test sample cards and maintaining an even or uniform air temperature distribution over the test sample cards. Preferably, the openings 626 are arranged in a manner such each of the openings 626 are oriented at an angle relative to the slots 614 of the carousel 604 such that the elongate openings 626 overlap at least two of the slots 614 of the carousel. This results in each card receiving air from at least two openings 626. Referring to FIGS. 6 and 7, the elongate openings 626 are preferably distributed in a symmetrical, ring-shaped pattern in substantial registry with the slots 614 in the carousel. Preferably, at least 10 such openings 626 are provided, and in the embodiment 24 such openings are shown. The elongated openings are preferred over a design such as small holes so as to minimize the risk of dust and dirt clogging the slots and interfering with the air flow. The particular design of the openings is determined by the particular air flow characteristics for establishing uniform air flow distribution and providing a substantially constant and even temperature distribution in the incubation station. The design of the carousel may of course affect the design of the openings 626.

Thus, other options are possible for the pattern and arrangement of the openings 626. One is an arrangement of the openings 626 in concentric circles in registry with the carousel, as shown in FIG. 12A. Another possibility is forming the openings 626 as a plurality of overlapping arcuate segments as shown in FIG. 12B. Other possibilities include rings of cross-shaped openings 626 (FIG. 12C), elongate arcuate openings in a spiral pattern (FIG. 12D), semicircular openings 626 arranged in a ring pattern (FIGS. 12E and 12F), a plurality of circular openings 626 arranged in concentric rings (FIG. 12G), and a plurality of "L"-shaped openings 626 arranged in a ring (FIG. 12H). What should be avoided is an arrangement in which a card in the carousel, with the carousel at rest, that substantially obstructs the air flowing out of any one opening in the air distribution cover plate 625, hence the angled design in FIG. 12 and the offset arcuate segments in FIG. 12B. Note that in FIGS. 12—12H, a card in a carousel card slot will only obstruct a relatively small portion of any particular opening 626. A primary goal of the design of the opening is that air flow out of the air distribution cover plate should be substantially independent of the presence or absence of a card in the carousel slot. Within these teachings, persons of skill in the art may arrive at other suitable configurations within the scope of the invention.

Figure 8:
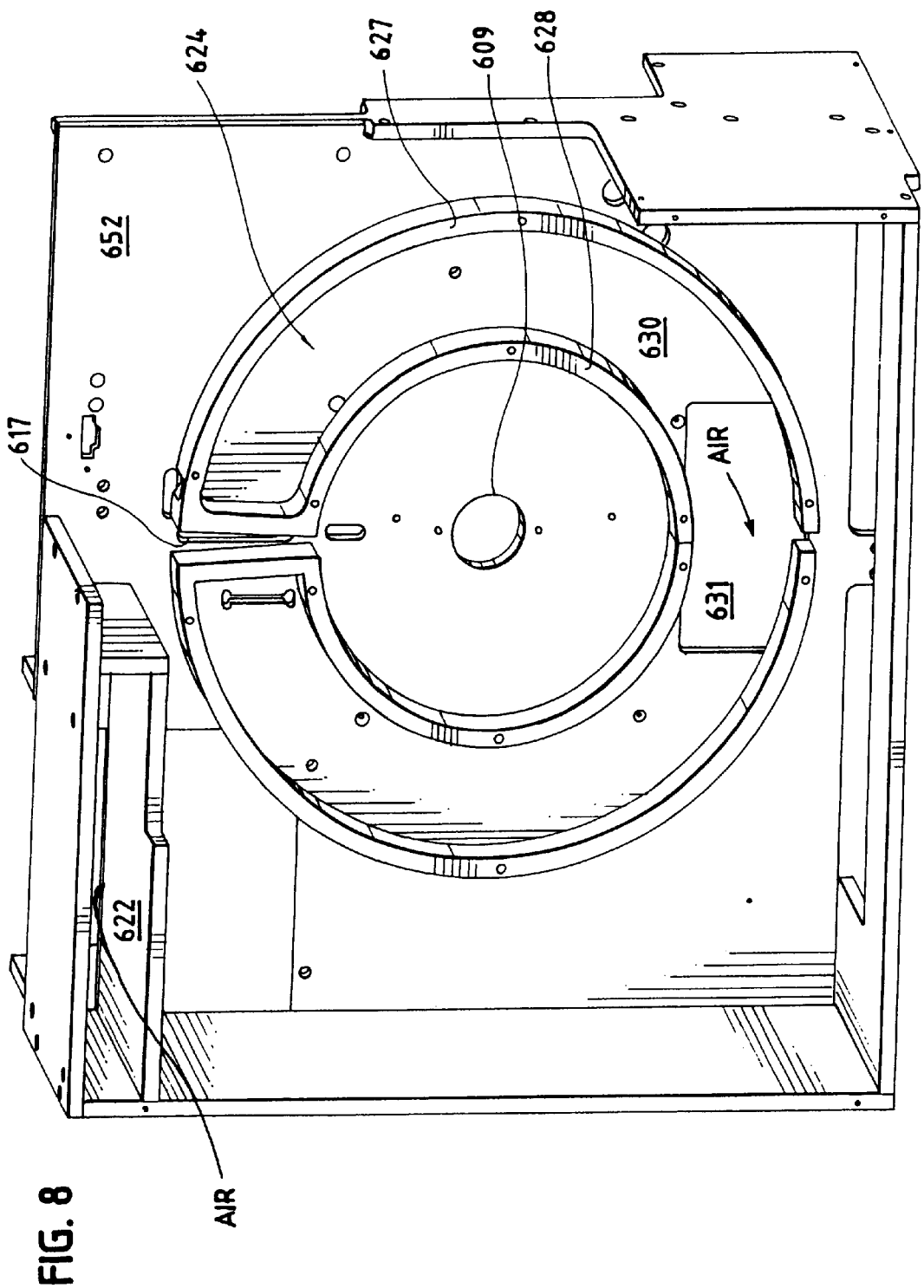
FIG. 8 is a perspective view of the incubation station of FIG. 7, with the air distribution cover plate of the air table removed in order to illustrate the internal structures of the air table.

FIG. 8 is a perspective view of the incubation station of FIG. 7, with the cover plate 625 of the air table 624 removed in order to illustrate the internal structures of the air table 624. The air table 624 consists of a pair of circular walls 627 and 628 that define and enclose a ring-shaped region 630 in registry with the carousel. An opening 631 at the lower portion of the bulkhead 652 allows warmed air from the rear of the bulkhead 652 to be introduced into the ring-shaped region 630. The gap 617 at the top of the air table is to allow the reciprocating driver 620 (FIG. 3) to move through an aperture in the bulkhead 652 and push the test sample cards out of the top of the carousel into the test sample card transport station 700 of FIG. 3.

FIG. 12 is an isolated, elevational view of one section 670 of the carousel positioned over the mounting plate 678, showing the angled relationship of the elongate openings 626 in the air distribution cover plate 625 of the air table 624 with respect to the slots 614 in the carousel.

Figure 9:
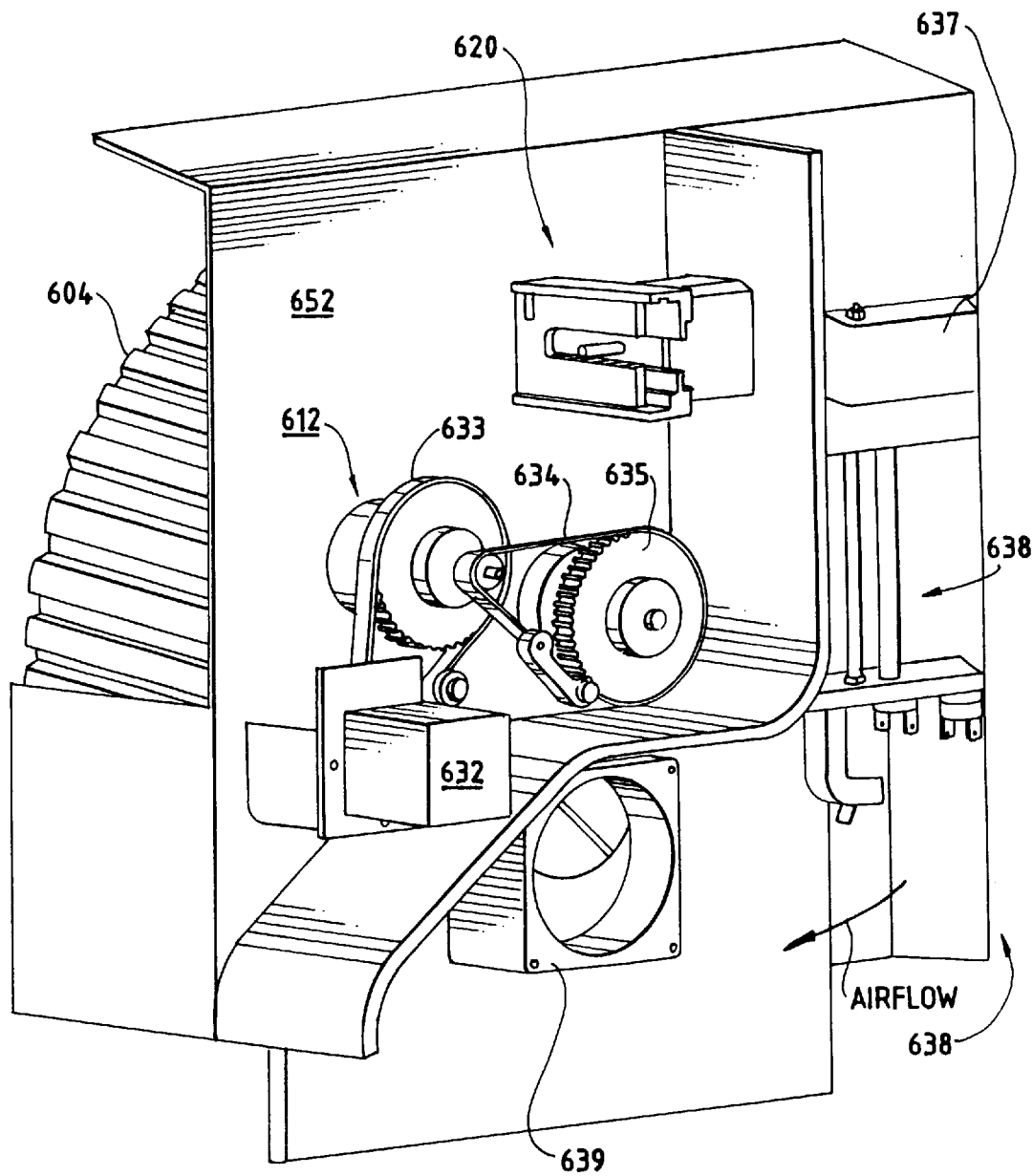
FIG. 9 is a perspective view of the rear portion of the incubation station with the cover panels removed, illustrating the drive system for rotating the carousel and the fan and heater assemblies that direct warm air through an aperture in the bulkhead into the air table of FIGS. 7 and 8 for distribution over the carousel.

FIG. 9 is a perspective view of the rear portion of the incubation station 600 with the cover panels covering the rear of the station 600 removed, illustrating the drive system 612 that rotates the carousel 614. The drive system 612 comprises a stepper motor 632, a first belt 633, a second belt 634 and a pulley 635 that is rotated by belt 634. The pulley 635 is connected to a shaft 611 (see FIG. 3) that passes through an aperture 609 in the bulkhead which is attached to and rotates the carousel 604.

A first fan 637 is positioned behind and below the air duct 622 (FIG. 6) which blows ambient air down over a heater assembly 638 which warms the air. The air inlet hole in the rear cover panel (not shown) is above the elevation of the fan 637. A second fan 639 is positioned immediately behind the aperture 631 (FIG. 8) and directs air warmed by the heater 638 through the aperture 631 in the bulkhead and into the air table 624 of FIGS. 7 and 8 for distribution over the carousel 604. Thermistors are provided, one in the rear of the bulkhead below the heater 638 and one behind the air distribution cover plate of air table 624 for controlling the operation of the heater and the temperature of the air exiting the air table 624.

Figure 10:
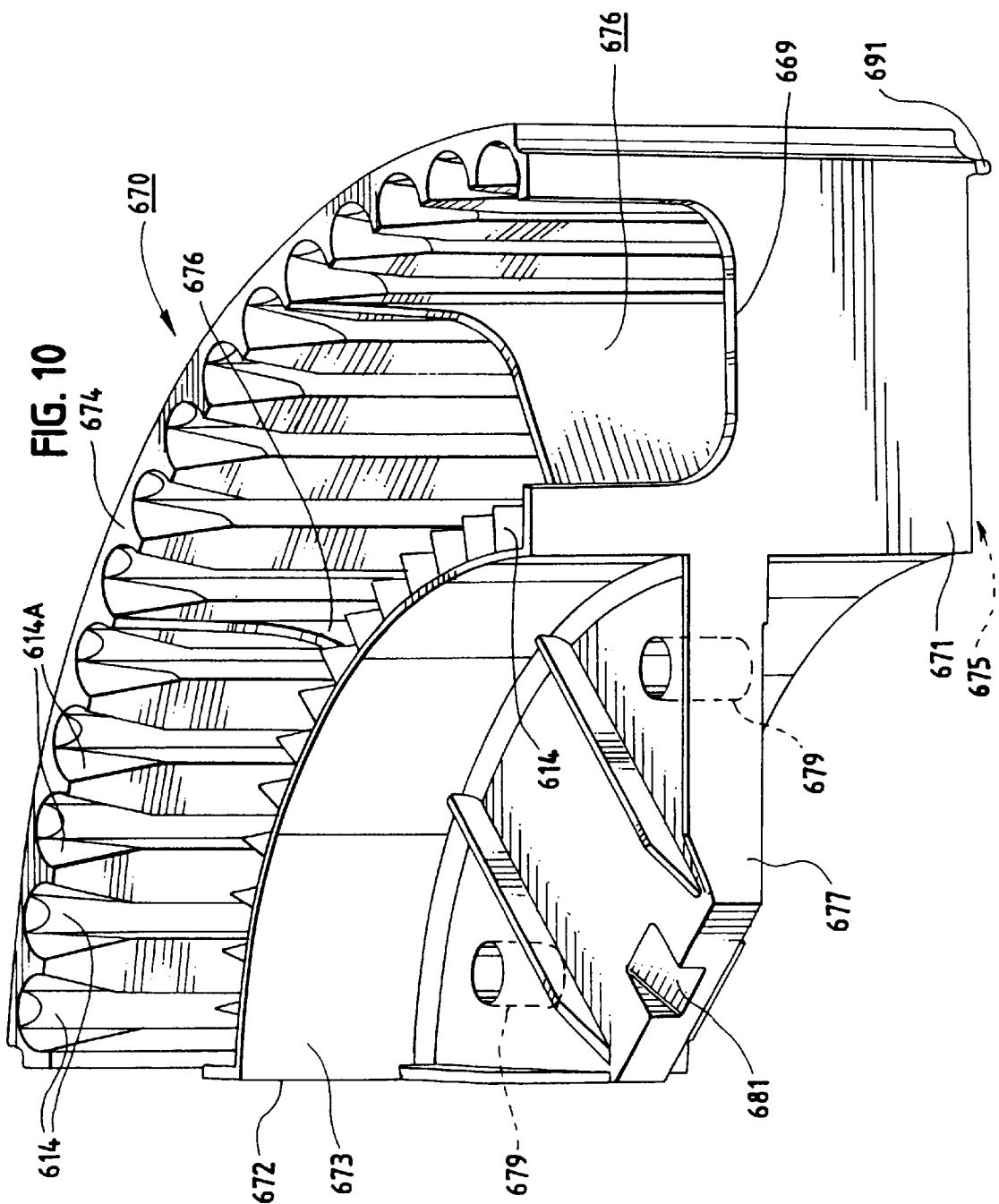
FIG. 10 is an isolated perspective view of one segment or section of the carousel in accordance with a preferred embodiment of the invention.
Figure 11:
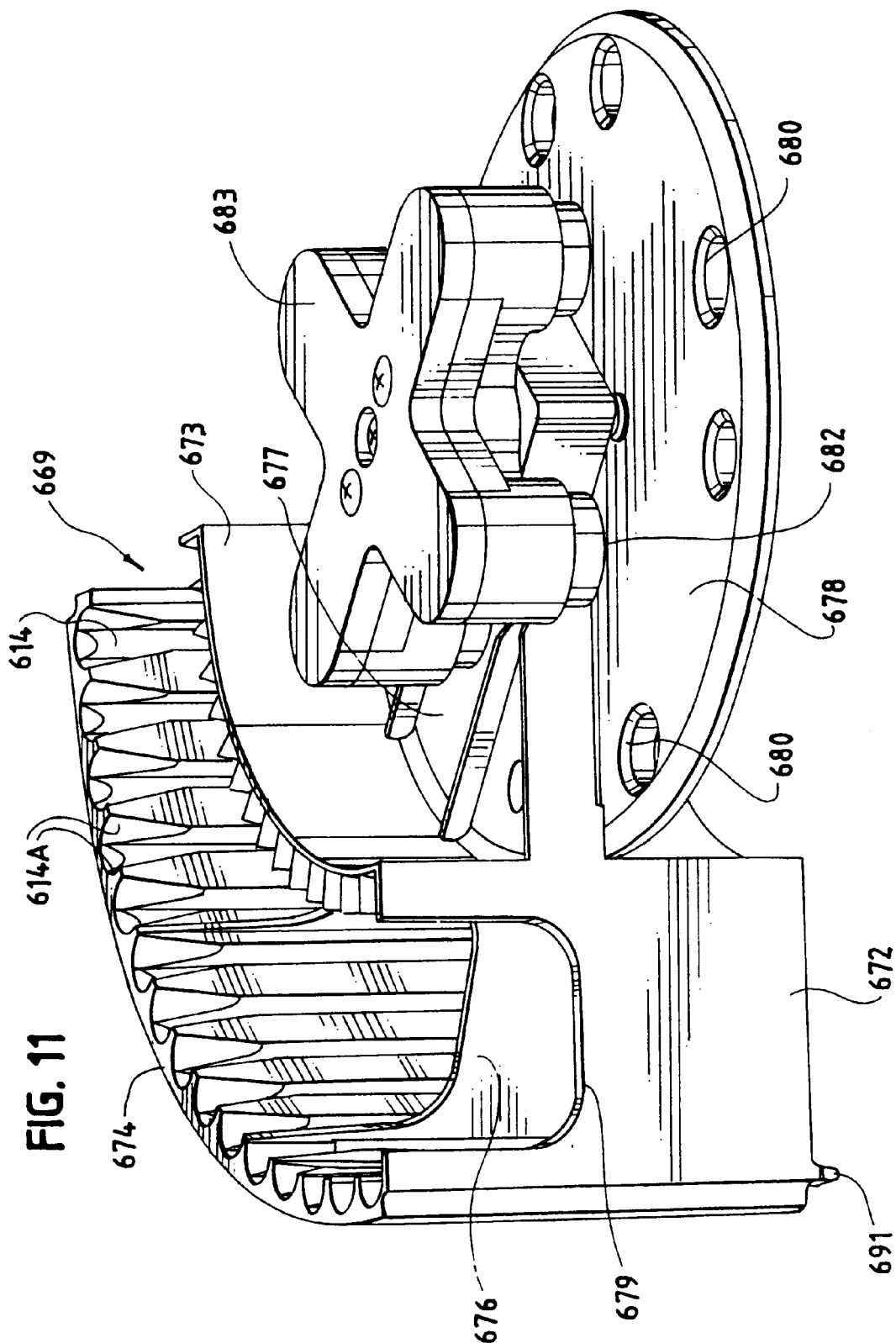
FIG. 11 is an isolated perspective view of one section of the carousel showing the mounting of the section to the mounting plate by a spring loaded pin assembly.

In a preferred embodiment, the carousel 604 is constructed as a plurality of discrete, separable arcuate carousel segments or sections, such as four pie-shaped segments, each referred to as a "quad" or a "quadrocell", each of the segments separately removable from the incubation station enclosure in order to facilitate easy removal of the carousel for clearing or maintenance. FIG. 10 is an isolated perspective view of one such segment 670 of the carousel 604. The segment comprises a first end wall 671, a second end wall 672, an inner arcuate wall 673, and a concentric outer arcuate wall 674. The rear side 675 portion is substantially open, allowing air to circulate from the slots 626 in the air distribution cover plate of the air table of FIG. 7 to freely pass over test sample cards placed in the slots 614. The slots 614 have opposed ramp faces 614A (FIGS. 10 and 11) to promote the easy insertion of the test sample cards into the slots 614. A least one reinforcing rib 676 is provided that extends between the inner wall 673 to the outer wall 674 to give adequate strength to the carousel segment 670 and improve moldability of the segment 670. Further, the end walls 672 are formed with substantial scalloped void regions 669, which has been found to improve the air flow over the test sample cards. The front surface of the carousel segment is spaced from the front cover panel of the incubation enclosure to allow efficient air return via duct 622 (FIG. 6).

A mounting flange 677 is provided integral with the inner wall 673 which is used to mount the segment 670 to a mounting plate 678 (FIG. 11) connected to the end of the drive shaft 609 (FIG. 3). The mounting flange 677 has a guide ramp 681 to assist in placement of a pair of downwardly depending cylindrical legs or projections 679 formed on the bottom surface of the flange 677 into a pair of corresponding holes 680 formed in the mounting plate 678. The segment 670 is held in place by the action of a spring loaded pin 682 positioned within a retaining hub 683 clamping the flange 677 against the mounting plate 678.

Figure 11A:
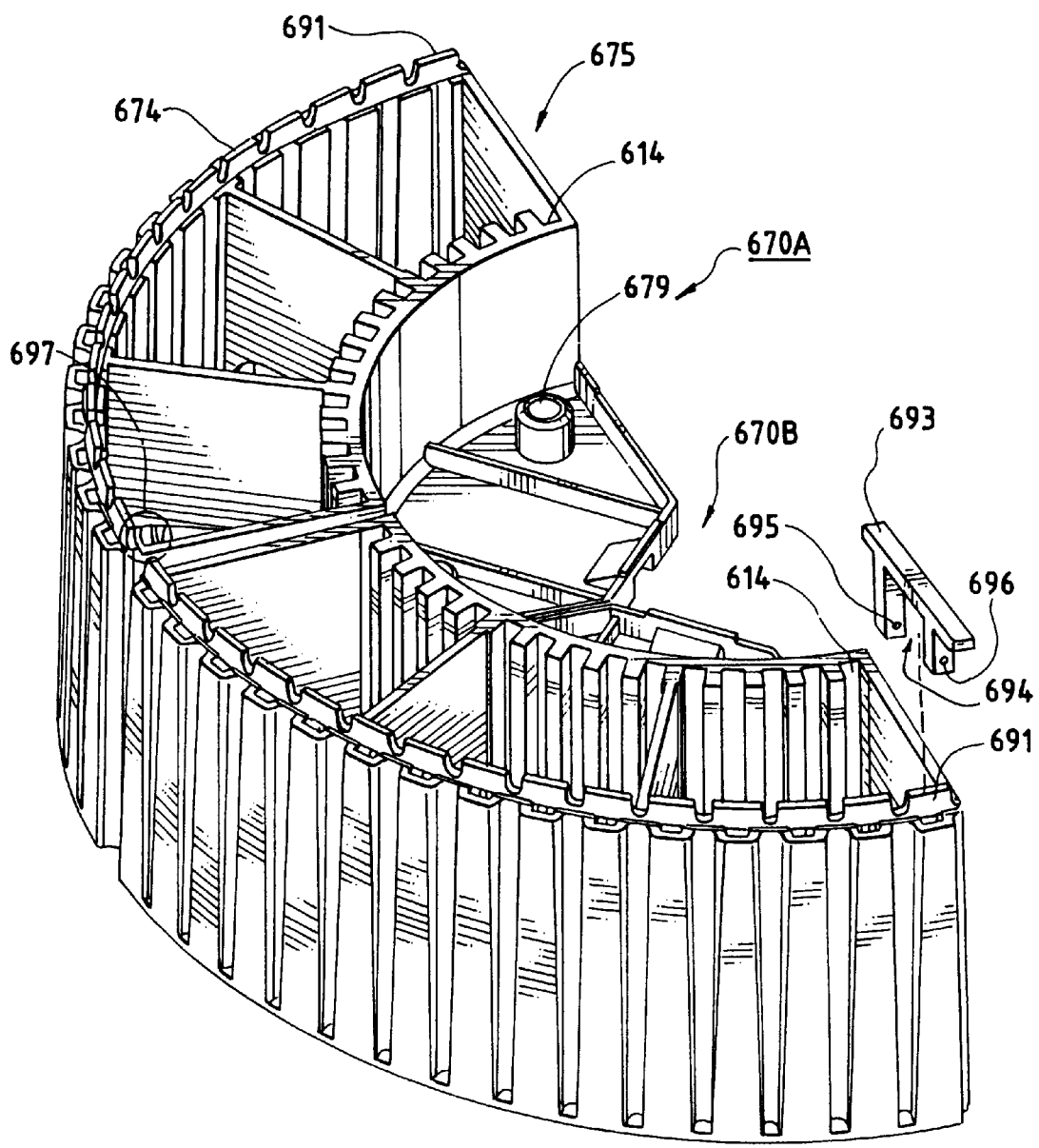
FIG. 11A is an isolated perspective of two carousel segments as seen from the rear, showing the positioning tabs used by an optical switch to correctly position the carousel slots to receive and eject test sample cards from the carousel.
Figure 11B:
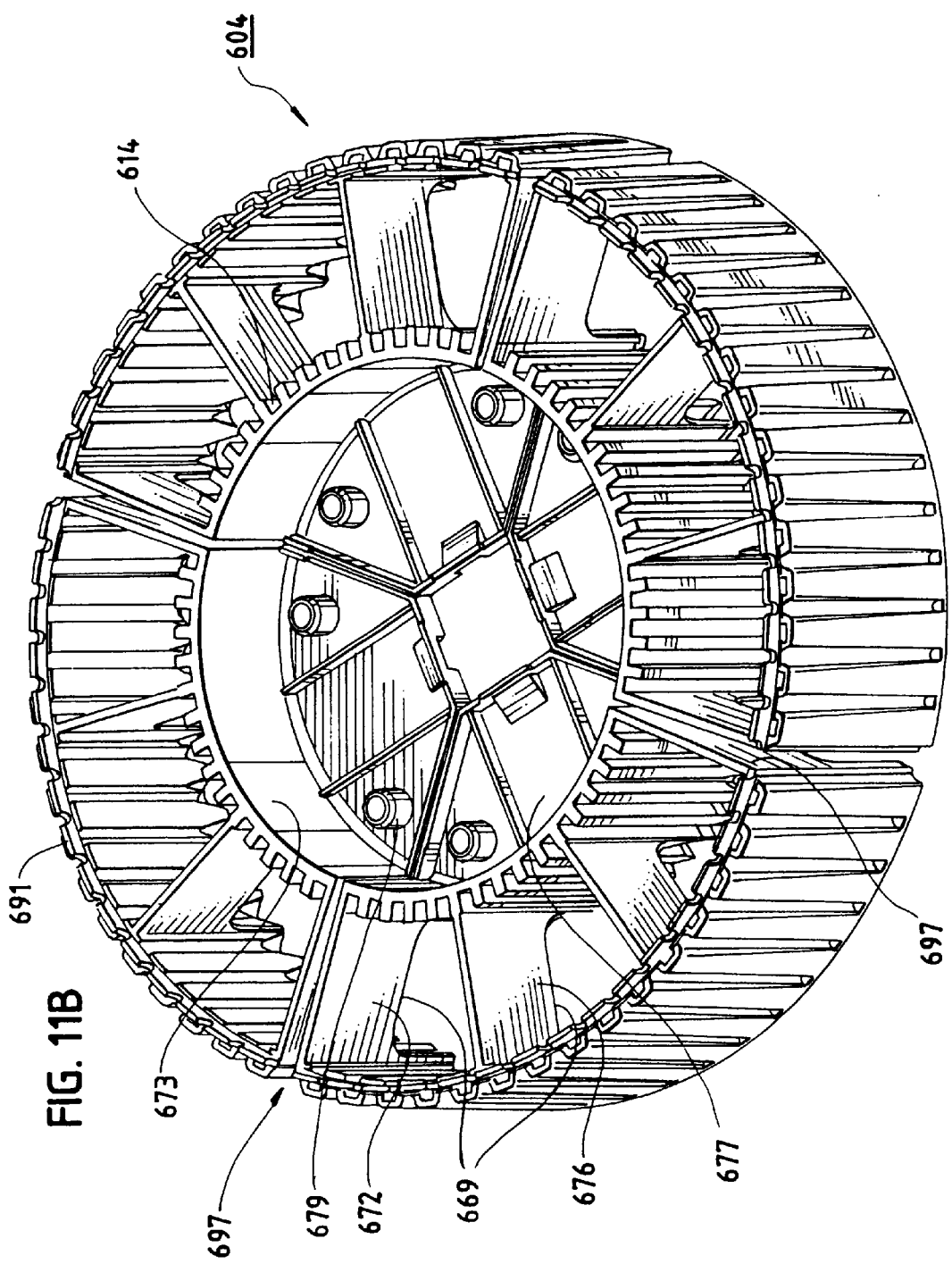
FIG. 11B is a perspective of the entire carousel as seen from the rear.

FIG. 11A is a perspective view of the rear of two carousel segment 670A and 670B in which a plurality of upstanding tabs 691 are provided on the rear surface 675 of the outer peripheral arcuate wall 674. FIG. 11B is a perspective view of the rear of an entire carousel 604. The tabs 691 are positioned in registry with the carousel slots 614. The tabs 691 are used in conjunction with an optical position sensor 693 comprising a slotted optical switch that is positioned adjacent to the bulkhead 652 (FIG. 8) within the incubation station immediately behind the rear surface 675 of the carousel such that the tabs 691 pass in the slot 694 between the emitter 695 and detector 696 of the optical position sensor 693 (FIG. 11A) as the carousel rotates. The optical position sensor 693 is mounted in any convenient position adjacent to the bulkhead such that the placement of a tab 691 between the emitter and detector results in the slots 614 of the carousel being correctly placed to receive a test sample card from the card loading mechanism 610 of FIG. 3, and correctly placed for the card ejection mechanism 648 of FIG. 17 and 18 to push a test sample card out of the slot 614 in the carousel. It is important that the optical interrupts are positioned such that there is a gap between the carousel segments 670A and 670B in the location 697.

Figure 14:
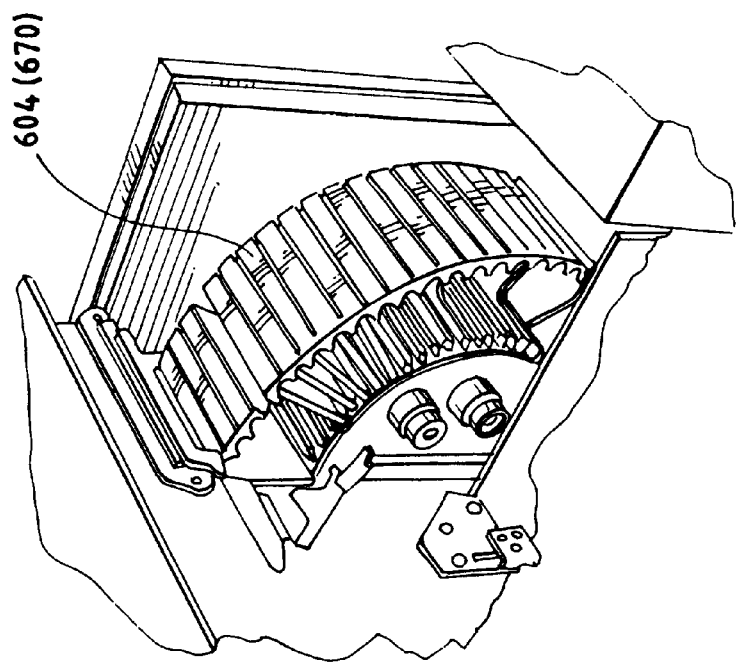
FIG. 14 is a perspective view of the section of the carousel installed.
Figure 13:
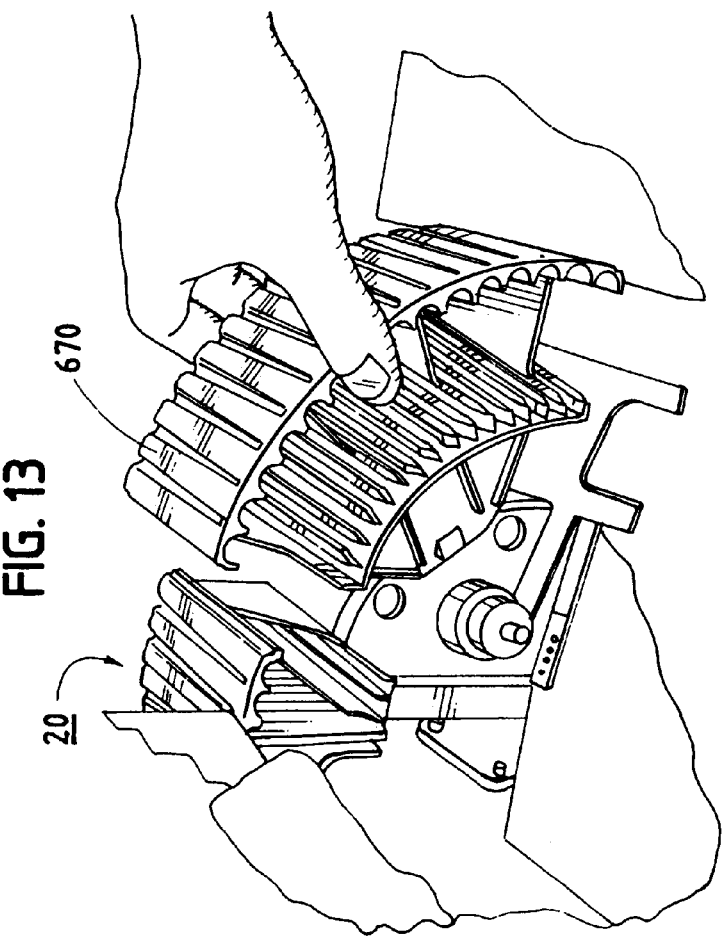
FIG. 13 is a perspective view of the carousel in an installed condition showing the easy manual removal and insertion of a section of the carousel from the instrument.

FIG. 13 is a perspective view of the carousel 604 in an installed condition showing the easy manual removal and insertion of a section 670 of the carousel 604 from the instrument 20. FIG. 14 is a perspective view of the section 670 of the carousel 604 installed.

Figure 15:
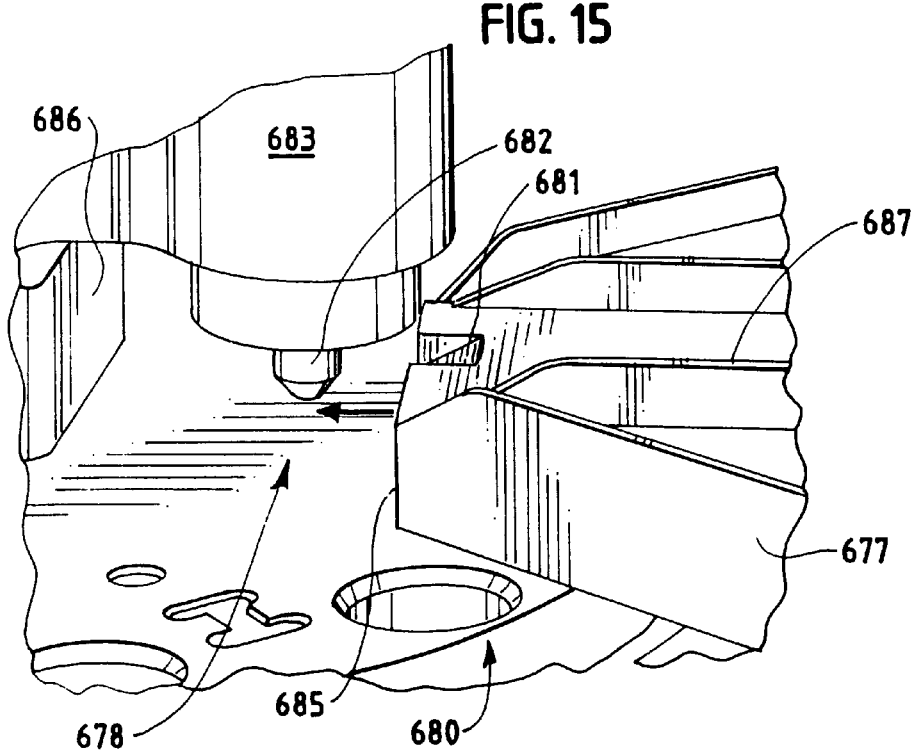
FIG. 15 is a detailed perspective view of the spring loaded pin, mounting table and flange of the carousel section just prior to insertion of the section.
Figure 16:
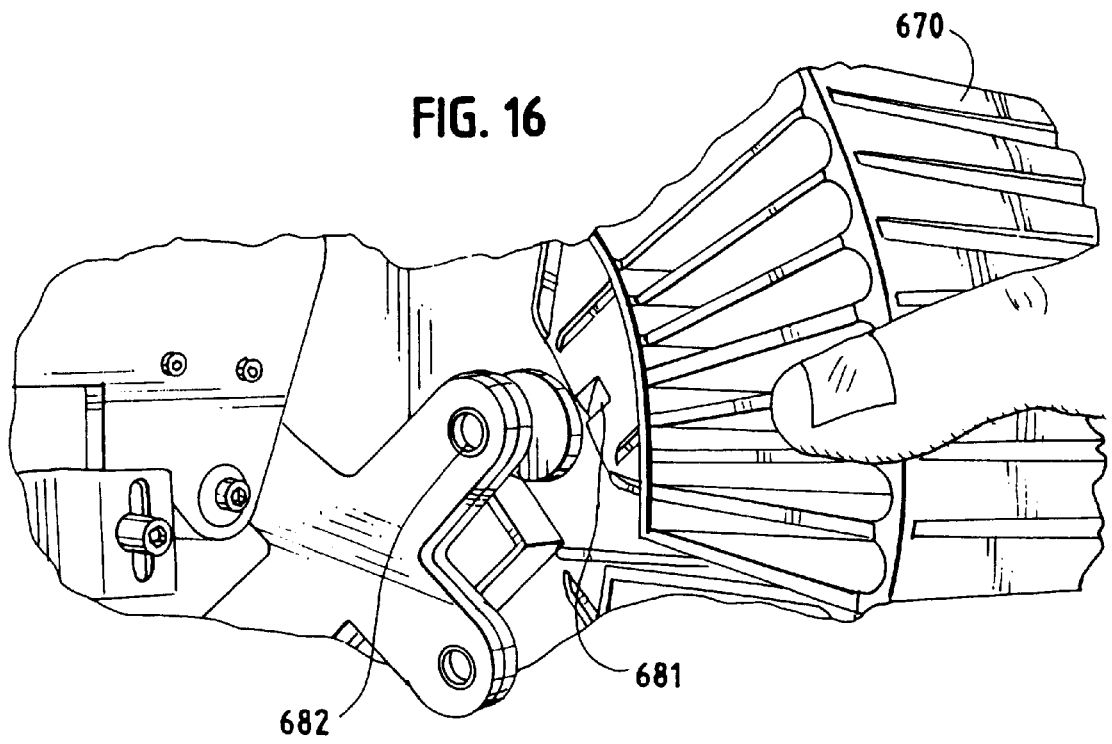
FIG. 16 is detailed perspective view of the spring loaded pin and carousel section as the carousel section is being inserted into the instrument.

FIG. 15 is a detailed perspective view of the spring loaded pin 682, mounting plate 678 and flange 677 of the carousel section 670. As the section is moved inwardly in the direction of the arrow towards the center of the mounting plate 678, the spring loaded pin 682 rides up the ramp 681 against the force of a biasing spring (not shown) inside the hub 683. The front surface 685 of the flange 677 abuts the flat planar portion 686 of the hub 683, positioning the cylindrical legs 679 (FIG. 10) into the holes 680. The spring loaded pin 682 then presses against the flat planar portion 687 of the flange 677 to lock it in place. FIG. 16 is detailed perspective view of a section 670 of the carousel being inserted, showing the ramp 681 in alignment with the spring loaded pin 682 immediately before the section 670 is locked into place.

FIG. 17 is a perspective view of a push mechanism 648 located at the top of the bulkhead of FIG. 6 that pushes the cards out of the slots in the carousel of FIG. 2 into the sample card transport system 706, 704, 710 and 718 of FIG. 1. The air table has been removed in order to better illustrate the push mechanism. FIG. 18 is a perspective view of the push mechanism as seen from the rear of the bulkhead. Referring to FIGS. 17 and 18, in order to place the card 28 into the sample card transport system 700, a rack and pinion push mechanism 648 is provided to push the card 28 out of the carousel 604. The push mechanism includes an alignment block 654 mounted to the bulkhead 652 and a driver 656 that reciprocates back and forth relative to the block 654. A motor 648 having a gear 662 is mounted behind the bulkhead 652. The teeth of the gear 662 cooperate with a set of teeth 658 on the driver 656, such that rotation of the gear 662 backwards and forwards causes the driver 658 to move in the direction shown by the arrow 664 (FIG. 18) in the space between a lower slot 666 and an upper slot 668 in the block 654. The end of the driver 656 is positioned in alignment with the top slot 614 in the carousel 604. When the driver 656 is operated by the motor 648 such that the driver 656 is pushed into the slot 614, the card 28 within the slot 614 is pushed out of the slot into the space between an internal slot in a ledge 718 and a drive belt 710. The optical detector 693 for the carousel tabs 691 (FIG. 11A) may be mounted above the block 654.

The card transport station 700 includes a cover plate 704, a card slot 706 defined between a drive belt 710 and the ledge 718 to move the cards 28 back and forth between the carousel 604 and the optical stations 802 and 804 of FIGS. 1 and 3. Further details on this drive system are set forth in greater detail in the above-referenced patent application of Mark J. Fanning et al. Ser. No. 08/604,672 which is incorporated by reference herein.

Figure 19:
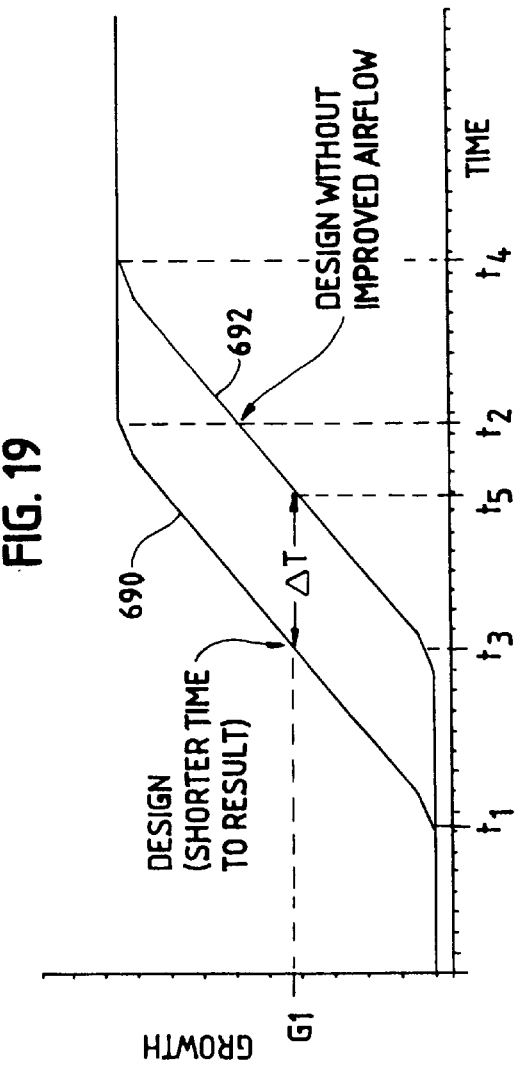
FIG. 19 is a graph of the growth curves of microorganisms in the wells of the test sample cards as a function of time for the incubation station and instrument of the preferred embodiment, as compared to the growth curves for the instrument without the improved air flow features.

The advantages of the improved air flow features described above compared to an incubation station without these features are illustrated in FIGS. 19–22. FIG. 19 is a graph of the growth curves of microorganisms in the wells of the cards as a function of time for the incubation station and instrument of the preferred embodiment described in FIGS. 6–18 (line 690), as compared to the growth curves for the instrument without the improved air flow features (line 692). Line 690 indicates that after a few hours of incubation, at time t1 the growth of the microorganism begins to increase at a steady rate until time t2, when the growth levels off. During the time between time t1 and time t2, the cards are moved in and out of the incubation station and shuttled back and forth to the optical stations for reading. At a population level of G1, the light transmittance characteristics have changed from an initial measurement at time t1 such that that a positive reading of the well would occur in the optical system at time t3.

It is also believed that the improved air flow techniques of the present invention improve oxygen transfer through the oxygen-transmissible tape that covers the wells of the card. Since the reactions occurring within the cards are typically aerobic reactions, increasing the supply of oxygen helps promote the reaction within the wells of the card and shorten the time needed to obtain a test result.

In a system without the improved air flow features resulting in zones of cooler temperatures in the vicinity of the card, the organism growth does not begin until about time t3, and reaches a maximum at time t4. The time at which a positive reading occurs at time t5. Time t5 is later than time t3 by an amount Δt, which could be as much as several hours. This shortening in the incubation time by the amount Δt was found to be the direct result of improving the air flow over the cards by adding a second fan 639 (FIG. 9) in the rear in the bulkhead opposite the opening 631 in the bulkhead (FIG. 8), adding the voids 669 in the end walls of the carousel segments (FIGS. 10 and 11), reducing the width of the carousel, opening the rear side portion of the carousel 604 to the air table 624, and providing the elongate slots 626 in the manner described above (see FIG. 7) in the air distribution cover plate of the air table.

Figure 20:
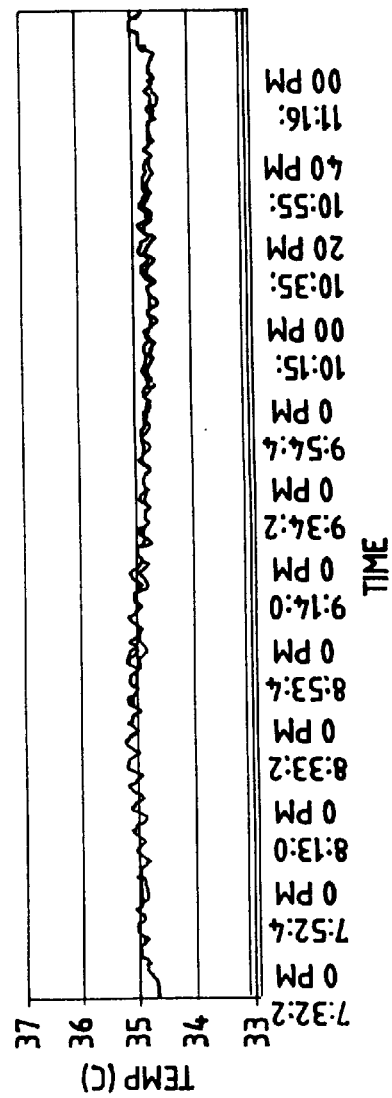
FIG. 20 is a graph of temperature as a function of time inside the incubation station for a four hour period, showing the very small temperature variation that occurs inside the incubation station in accordance with the invention.

FIG. 20 is a graph of temperature as a function of time inside the incubation station for a four hour period, showing the very small temperature variation that occurs inside incubation station in accordance with the invention. Without the above-referenced air flow improvements, air temperature variation away from the desired temperature of 35.5 degrees C. in the incubation station was on the order of several degrees C., whereas with the improvements it was reduced to less than 1 degree C. over a four hour period. This even temperature characteristic would be expected to be maintained for longer incubation periods, such as 12 or 18 hours.

Figure 21:
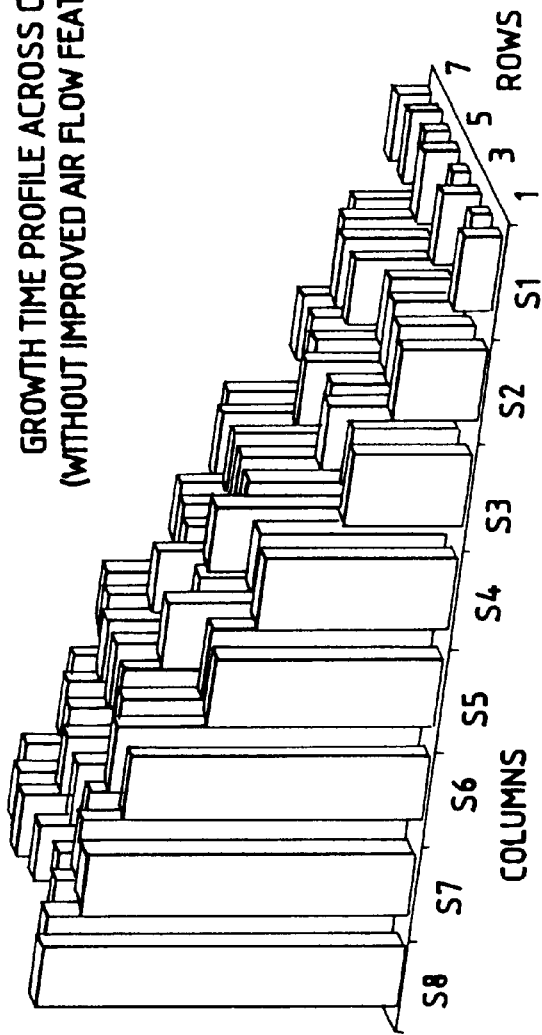
FIG. 21 is a graph of the growth time profile for dispersed wells in a test sample card incubated in an incubation station that does not have the improved air flow features described herein, showing the undesirable wide variation in growth time across the cards which is directly attributable to poor air flow characteristics.

FIG. 21 is a graph of the growth versus time difference profile for sample wells in a test sample card incubated shown in FIG. 3, in an incubation station that does not have the improved air flow features described herein, for example, without the second fan, without a reduced width quadrocell, without the open rear of the carousel, and using a single opening for air distribution instead of slots in the cover plate of the air table (FIG. 7). The growth profiles of some of the bacteria or antibiotic combinations are directly related to the temperature (and air flow)in the slots of the carousel, with greater temperatures and air flow may result in faster growth and lower temperatures and less air flow may result in slower growth. Even temperature and air flow and hence growth across all the wells is the desired result. FIG. 21 illustrates the undesirable wide variation in growth time across the cards, with the wells at in the eighth or left hand column S8 having markedly longer growth times as compared to the wells in the first column S1.

Figure 22:
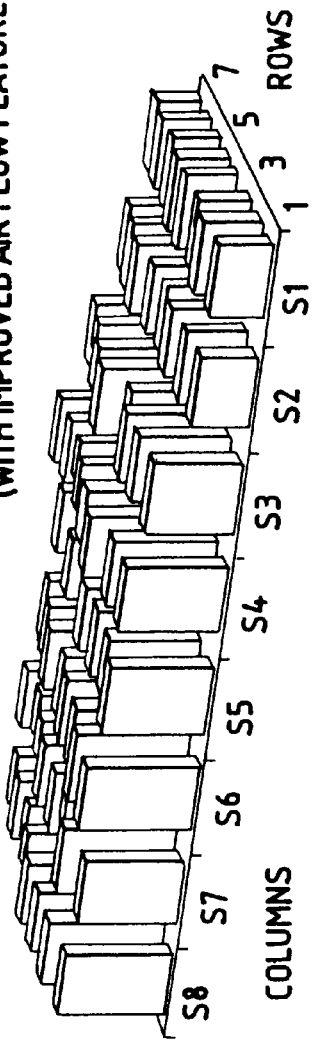
FIG. 22 is a graph of the growth time profile for dispersed wells in a test sample card incubated in an incubation station that has the improved air flow features described herein, showing the minimal variation in growth time across the cards, a desirable result of the invention.

FIG. 22 is a graph of the growth time profile for sample wells in a test sample card incubated in an incubation station that has all of the improved air flow features described herein, showing the substantially reduced variation in growth time across the cards. While columns S3–S8 exhibit slightly longer growth times as compared to column S1, the difference is much less pronounced than that shown in FIG. 21. The difference in growth time profiles shown in FIG. 22 would not be expected to adversely impact the sample testing procedure. Further, by virtue of the rotation of the carousel at a rate of one revolution per 15 minutes, and all incubation times being on the order of more than one hour, each card in the carousel 604 would be expected to exhibit the temperature pattern and hence growth profile shown in FIG. 22.

It is contemplated that various degrees of air flow improvement and even temperature distribution would be observed with various combinations of each of the specific air flow improvement features described above, and not all of them need necessarily be adopted. Thus, the invention should not be considered limited to incorporation of all of the features in any given system. The particular requirements of the incubation system at issue, the geometry of the carousel and its relation to surrounding structures, the available space, the specifications of the fan and designed temperature, and still other considerations may impact the selection of features.

Card Detection Device Detailed Description

In FIG. 3, a card separation device comprising a wheel 94 attached to an arm that pivots about a pin 98 is shown. As the boat 22 and cassette 26 pass by the wheel 94, the wheel 94 rocks the cards 28 back within the slots of the cassette 26 to expose the upper surface of the card 28 and bar code affixed at this location to an optical reader 90 located forward of and above the card in the machine.

Figures 26, 27, 28:
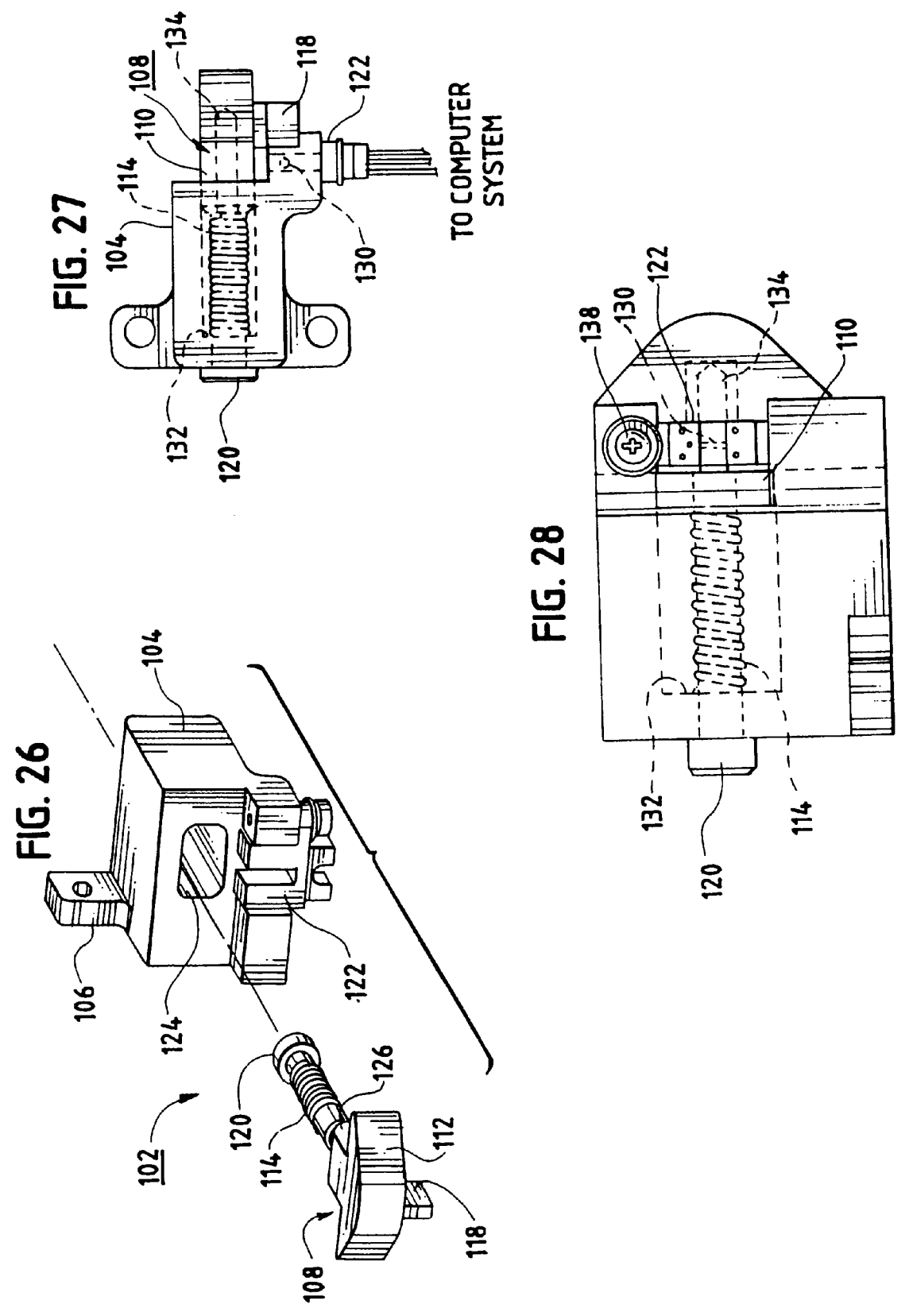

FIG. 23 is an isolated perspective view of an alternative and more preferred card separation device 102 that is also capable of card detection. FIG. 24 is a side elevational view of the card separation and detection device 102. FIG. 25 is a front elevation view of the device 102. FIG. 26 is an exploded perspective view of the device 102.

Referring to these figures, in conjunction with FIGS. 1, 2 and 3, the device 102 is mounted to a flange off of the center mount 34 in essentially the same manner and location as shown for the device 94 in FIG. 3, in a position "upstream" of the reading device 90 and in optical alignment with the reading device 90. The card separation and detection device 102 includes a housing 104 having flanges 106 that are attached to structures in the instrument (such as cross-member 92 or mounting flange 91 depending from cross-member 92 in FIG. 3) in proximity to the pathway that the cards 28 move along within the instrument. In FIG. 3, the motion of the boat 22 on the lower left hand side of the illustration is into the page, thus the card separation device separates the cards 28 as the cards are moved past the device so that the optical reader 90 can read bar codes positioned at the top of the card facing the optical reader 90.

The device 102 includes an actuator 108 reciprocating relative to the housing 104 between a first or extended position and a second or retracted position. The actuator 108 has a head portion 110 with a first card contact surface 112. When the card 28 contacts the card contact surface 112 as the card 28 is moved past the device 102, the actuator 108 is moved by the card from its extended position, against the force of a biasing spring 114 surrounding a threaded shoulder screw 120, to a retracted position relative to the housing 104 in the manner suggested by the arrow in FIG. 23.

The actuator 108 carries an optical interrupt flag 118 on the lower surface 120 of the head portion 110. When the actuator 108 is moved to the retracted position, the flag 118 is moved into the optical path of an optical detector 122. The optical detector 122 is mounted to the housing 104 immediately below the actuator 108. The movement of the flag 118 into the optical path of the detector 122 triggers the optical detector 122, and sends a signal to the central computer system for the instrument indicating that a card was detected by the device 102.

The action of the card 28 contacting the surface 112 actuator 108 also results in a movement of the card relative to the cassette and the automated reading station 90 such that the indicia or bar codes positioned on the top edge of the cards 28 are better positioned for reading by the reader 90. Specifically, the card is rocked back in the slot in the cassette 26 to an angle, and moved away from the card in front of it in the cassette 26, such that the bar code or other indicia is clearly exposed to the reader 90. As the card is moved further past the actuator 108, the actuator 108 is moved by the biasing spring 114 back to its first or extended position, at which time a second card contact surface 124 contacts the card 28 and pushes the card forward in the slot in the cassette 26. This helps separate one card from the next in the cassette.

In FIGS. 23–26, the flag 118 is shown attached to the actuator 108 with the optical detector 122 mounted to the housing 104. These positions could be reversed, but with the same result achieved of detection of a card when the actuator is moved to the retracted position.

As shown in FIG. 26, the actuator 108 reciprocates in an oval aperture 124 in the housing 104. The shoulder 126 of the actuator 108 is given an oval cross-sectional shape and dimension so as to fit inside to the aperture 124 and not result in any rotational or side to side translational motion.

FIG. 27 is a side view of the device 102 in an assembled condition, partially in section, showing the position of the threaded shoulder screw 120 within the body of the housing 104, and the flag 118 on the actuator relative to the optical sensor 122 when the actuator 108 is in the extended position. Note that when the actuator 108 is moved to the retracted position, the flag 118 is moved into the optical path 130 of the optical sensor 122. Note also in FIG. 27 that the spring 114 has one end thereof that seats against the rear surface of the head portion 110, and a second end that seats against an inner vertical wall 132 in the housing 104. The threaded shoulder screw 120 has a tip 134 that is connected to the head 110. A clearance exists between the head 110 and the walls of the aperture 124 (see FIG. 26) allowing the head 110 of the actuator 108 to freely move back and forth within the aperture 124.

FIG. 28 is a bottom plan view of the device, partially in section, showing the position of the shoulder screw 120 within the housing 104. A screw 138 mounts the optical sensor 122 to the housing 104 in proximity with the flag 118 such that the flag 118 reciprocates with the actuator 108 into the space between the source and detector of the optical sensor 122.

Persons of skill in the art that variation may be made to the preferred and alternative embodiments described above without departure from the true spirit and scope of the invention. This true spirit and scope is determined by the appended claims, to be interpreted in light of the foregoing.

We claim:

1. A carousel for receiving a plurality of flat, thin test sample cards, said carousel for placement in an incubation enclosure, comprising:
   a plurality of discrete, separable carousel segments, each of said segments separately removable from said enclosure,
   each of said discrete, separable carousel segments comprising:
      a first end wall,
      a second end wall, said first and second end walls defining a portion of an arc;
      an inner wall and an outer wall concentric with said inner wall, said inner and outer walls each connected to said first and second end walls;
      a plurality of individual elongate slots formed and extending between said first and second end walls and between said inner and outer walls and closely spaced in an array, said slots shaped and arranged in said array in a manner for receiving said test sample cards therein, said carousel segments having an open rear face thereof for allowing the flow of temperature controlled air over said test sample cards received in said slots in said incubation enclosure, and
      an inwardly disposed mounting means connected to said inner wall for securely fastening said separable carousel segment to a permanent structure in said incubation enclosure and enabling release of said separable carousel segment from said permanent structure and enabling said carousel segment to be removed from said incubation enclosure.

2. The carousel of claim 1, wherein said first and second end walls each are characterized in having a substantial void formed therein so as to improve air flow over said test sample cards.

3. The carousel of claim 1, wherein said carousel further comprises a centrally located mounting plate and a means for securing said discrete, separable carousel segments to said mounting means.

4. The carousel of claim 1, wherein each of said discrete, separable carousel segments further comprise at least one reinforcing rib extending from said inner wall to said outer wall.

5. The carousel of claim 1, wherein said discrete, separable carousel segments comprises four of such segments, each forming a quadrant of said carousel, with each of said quadrants comprising a peripheral arcuate segment of said carousel.

6. A carousel for holding a plurality of test devices within an enclosure of an incubation station, said test devices comprising a substantially flat, thin test sample card body comprising at least one reaction well for containing a combination of a test sample and a reagent, comprising:
   a plurality of discrete, separable carousel segments, each of said segments separately removable from said enclosure and insertable into said enclosure for attachment therein to a permanent part of said incubation station,
   wherein each of said discrete, separable carousel segments comprise first and second end walls, said first and second end walls defining a portion of an arc,
   an inner wall and an outer wall concentric with said inner wall, said inner and outer walls connected to said first and second end walls, and
   a plurality of elongate slots formed between said first and second end walls and between said inner and outer walls, said slots arranged in an array of closely adjacent elongate slots and shaped for receiving said test devices; and wherein said first and second end walls each are characterized in having a substantial void formed therein so as to improve the flow of air within said incubation station over said test devices within said slots.

7. The carousel of claim 6, wherein each of said carousel segments further comprises a means for engaging said carousel segments to said permanent part of said incubation enclosure.

8. The carousel of claim 1, wherein said test sample cards comprise substantially flat and thin test sample devices.

9. A carousel for holding a plurality of test devices within an enclosure of an incubation station, said test devices comprising a substantially flat, thin test sample card body comprising at least one reaction well for containing a combination of a test sample and a reagent, comprising:

a carousel body insertable into said enclosure for attachment therein to a permanent part of said incubation station, said carousel body comprising an inner wall and an outer wall concentric with said inner wall, a front face and a rear face, said rear face substantially open and free of obstructions to thereby allow warm air to flow over said test devices;

said carousel body further comprising a plurality of elongate slots extending between said inner and outer walls, said slots arranged in an array around said carousel body, each of said slots having a shape adapted for receiving one of said test devices therein; and wherein said carousel body further comprises a plurality of transverse walls extending between and connecting said inner wall and said outer wall, each of said walls characterized in having a substantial void formed therein so as to improve the flow of air within said incubator station over said test devices within said slots.

* * * * *